United States Patent [19]

Weibel et al.

[11] Patent Number: 4,923,981

[45] Date of Patent: May 8, 1990

[54] USE OF PARENCHYMAL CELL CELLULOSE TO IMPROVE COMESTIBLES

[75] Inventors: Michael K. Weibel, Redding, Conn.; Chester D. Myers, Toronto, Canada

[73] Assignees: SBP, Inc., Philadelphia, Pa.; SLR Inc., Mississauga, Canada; a part interest

[21] Appl. No.: 334,596

[22] Filed: Apr. 6, 1989

Related U.S. Application Data

[63] Continuation-in-part of Ser. No. 62,445, Jun. 15, 1987, abandoned, which is a continuation-in-part of Ser. No. 512,940, Jul. 12, 1983, Pat. No. 4,831,127, which is a continuation-in-part of Ser. No. 414,931, Sep. 3, 1982, abandoned.

[51] Int. Cl.$^5$ ............... A61K 47/00; A61K 31/715; A23K 1/00; A23L 1/24
[52] U.S. Cl. .................................. 536/56; 426/602; 426/605; 426/615; 424/439; 424/441
[58] Field of Search ............ 426/615, 602, 605; 424/439, 441; 536/56

[56] References Cited

U.S. PATENT DOCUMENTS

| | | | |
|---|---|---|---|
| 3,023,104 | 2/1962 | Battista | 426/660 |
| 4,165,998 | 8/1979 | Adams et al. | 424/439 |
| 4,414,198 | 11/1983 | Michaelson | 424/441 |
| 4,629,575 | 12/1986 | Weibel | 536/128 |

Primary Examiner—Ronald W. Griffin
Attorney, Agent, or Firm—Lieberman, Rudolph & Nowak

[57] ABSTRACT

Improved comestibles including foods and drugs are provided, incorporating parenchymal cell cellulose. Improved properties, including physicochemical, rheological and nutritional properties result from such incorporation. Stabilized dispersions, emulsions, foams and frozen materials can preferably be provided through employment of the preferred embodiments.

30 Claims, 7 Drawing Sheets

FIG. 6
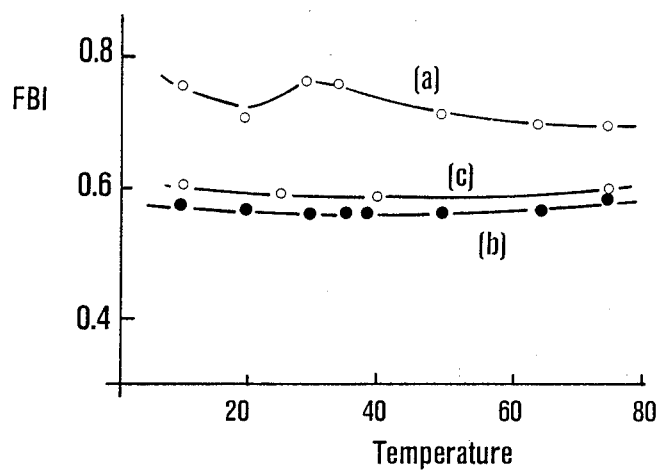
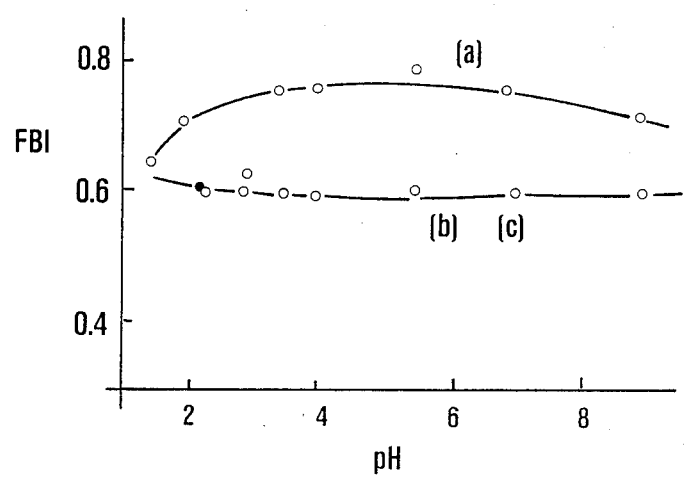
FIG. 7

USE OF PARENCHYMAL CELL CELLULOSE TO IMPROVE COMESTIBLES

CROSS-REFERENCE TO RELATED APPLICATIONS

This application is a continuation-in-part of U.S. patent application, Ser. No. 062,445, filed June 15, 1987 now abandoned. Ser. No. 062,445 is a continuation-in-part of Ser. No. 512,940 filed July 12, 1983, now U.S. Pat. No. 4,831,127, which, in turn, is a continuation-in-part of U.S. patent application, Ser. No. 414,931, filed Sept. 3, 1982, now abandoned. Each of the foregoing applications is incorporated herein by reference.

BACKGROUND OF THE INVENTION

1. Field of the Invention

This invention relates to comestibles. In accordance with the particular embodiments, comestibles are improved through the addition thereto or the incorporation therein of parenchymal cell cellulose (PCC) in amounts sufficient to effect such improvement. This invention is also directed to methods for the improvement of comestibles through the inclusion of parenchymal cell cellulose. The invention is also directed to methods for the preparation of drugs through the incorporation of parenchymal cell cellulose therein and also to the drugs thus prepared. In accordance with the present invention, foods and drugs which, for the purposes of this specification are included in the term "comestible," are improved by having their physical and physicochemical properties improved through the addition of PCC. In addition, it is now possible to prepare comestibles, including foods and drugs having improved cost factors, improved physical processing capabilities, lower cholesterol level, lower caloric level, enhanced flavor, and other beneficial properties.

2. Background of the Related Art

There are various functional properties that define a food in addition to flavor. That which is referred to as "texture" provides a major distinguishing feature for most foods. Texture is an important parameter that controls the desirability of food. A good steak is characterized by a suitable "yield" upon biting into it. Most puddings are similarly characterized by a proper "yield", but of a different strength. For those beverages that are relatively thick or more viscous, it is desirable that they be shear thinning, i.e., that the viscosity becomes lower in the throat during swallowing than is experienced at the lower shear rates in the mouth. Viscous beverages that are not shear thinning are either slimy, (Szczesniak and Farkas, *J. Food Sci.* 27, 381 (1962)), or quickly satisfy.

Spreads, butter, margarine, mayonnaise, and the like are also defined according to their textural properties. Ease of spreading with a knife is important, as well as the required mouthfeel properties. Salad dressings must be pourable from a bottle, yet the dressing must cling to the salad components. Different dressings have different pouring properties and different tendencies to cling.

Ice cream and butter textures are partly derived from the melting of the ice crystals and butter fat, respectively; these represent other types of mouthfeel properties—for example, the cooling from the ice melting, or the coating of the mouth by the butterfat.

Generally, heavier or thicker textures are achieved by increasing the solids content, or by maximizing attractive forces between individual components so that a structure is developed, i.e., some sort of gelation. This latter is achieved through changes in pH, salt levels, or the addition of certain other components. Thicker mayonnaise may be achieved with high levels of emulsified oil particles, or by the addition of carbohydrates that partly cross-link to form a partial gel. Xanthan gum is commonly used for this sort of cross-linking. In this regard, xanthan gum is dramatic in its behavior because, not only does it give a solubilized network, but it also forms colloidal aggregates whose breakup under shear contributes to yield point and to shear thinning—for example, see Pettitt, *Polysaccarides in Foods,* Butterworths, 1979; Sanderson, *Prog. Fd. Nutr. Sci.,* 6, pp. 77-87 (1982). Salad dressings are thickened with higher levels of herbs and other solids, by the addition of carbohydrates (again usually xanthan gum), or by adding materials that increase attraction between components. The latter are often surface active materials such as propylene glycol alginate. Milk solids, cocoa particles, emulsion oil/fat droplets, and so on are frequently employed as space fillers. Microcrystalline cellulose, such as the commercially available Avicel ® materials, has become recognized as a "Gold Standard" for this function. While it is very finely divided, its chief functionality results from the needle shape of the crystal and the ability of these crystals to interact with each other to set up a structure. Thus, a yield point is demonstrated at relatively low levels and shear thinning is a characteristic feature, McGinley et al, *Gums and Stabilizers for the Food Industry,* 2, Pergramon (1984).

The measurable parameters of texture are rheological in nature. Thus, viscosity (resistance to flow, i.e, resistance to irrecoverable deformation) and elasticity (resistance to recoverable deformation) are the fundamental measurements. Since each food has various viscous and elastic components, the food technologies resorts to composite evaluations that are related to viscosity and elasticity, but which do not completely define each individual rheological component. In addition to rheological measurements providing a definition of food texture, they also provide, in many cases, an indication of the physical stability of a food. The latter is especially important for those foods that are composed of two or more immiscible phases. An emulsion such as mayonnaise is one such system. Oil is dispersed into very small droplets as a disperse phase, and the interstitial spaces are filled with an aqueous continuous phase. Creaming, flocculation or coagulation, and coalescence are the three principal mechanisms of destabilization that must be minimized for any food emulsion product of technological importance.

All of these processes are slowed by formulations that provide a type of rheological mechanical barrier. Thus, high viscosity slows creaming and flocculation. Elasticity is the result of structure derived from the net forces between individual components resulting in a preferred arrangement of components. It is sufficient that there be a skeletal network of structure with interstitial spaces being filled with the remaining unstructured materials. Distortion (stress) of this arrangement by an external force (strain) can be accommodated without deterioration, depending on the extent of the distortion both in time and strength. Thus, the elasticity of the exterior of the oil droplets of a mayonnaise allows for spooning, spreading, etc. without disruption of the surfaces of the individual oil droplets —coalescence is thwarted as a result. An important feature of the return to the equilibrium structure after removal of the externally applied deformation is the length of time required, i.e., the relaxation time.

Instead of measuring true viscosity or of fully characterizing the elasticity, conventional measurements have centered on the use of rotational viscometers that give an apparent viscosity and an indication of elastic structure. This is provided by a rotating bob whose speed of rotation is controlled to provide a range of deformation rates called "shear rates"; the resulting stress is noted as a function of this shear rate. At low shear rates, flow may not begin until a certain amount of energy has been exceeded—this is the yield point of the material and reflects a type of structure that must be disrupted to allow flow to occur. As shear rate is increased, other structure may be only partly disrupted and likely reverses to its equilibrium position as fast as it is destroyed. Hence, the measured stress values are higher than that which would be observed from simple viscous flow in the absence of structure. As shear rate is increased still further, progressively greater proportions of structure are destroyed and the length of time required for reversal is greater than allowed by the shear rate. The stress is observed to decrease with the increased shear rate, and at some high shear rate, all structure may be obliterated. Finally, the observed stress that results from only viscosity is measurable. These very high shear rates are often technologically unimportant. The yield and the degree of shear thinning are directly relevant to the rates of shear experienced during mastication, pouring, whipping, spreading, etc. and, therefore, an apparent viscosity at a particular shear rate is useful. Instrumentally, stress is measured as a function of shear rate (the "flow curve"), and from this information is calculated: (i) the yield; (ii) the degree of shear thinning; and (iii) a viscosity at a defined rate of shear. The yield gives an estimate of the semisolid or gel-like nature of the material, the shear thinning indicates the range of structural heterogeneity (different relaxation times), and the apparent viscosity gives an indication of the simple viscous flow behavior. The Casson model (square root of stress vs square root of shear rate) may be used to estimate the yield values. The power law plastic [log (corrected stress) vs log (shear rate)] is then used to estimate the degree of shear thinning via the "flow behavior index" where values of 1 indicate Newtonian behavior and values of less than 1 indicate shear thinning. For this model, the apparent viscosity is determined at a shear rate of 1 sec$^{-1}$ (consistency coefficient). In this formula, corrected stress is the measured stress minus the yield value. Shear thinning is usually desirable in foods to facilitate mastication, swallowing, and processing, and to avoid sliminess.

Since relatively low rates of shear are used for flow curves, it is also useful to use a method that examines structures that have shorter times of relaxation. That structure with long times of relaxation derives from interaction between colloidal size moieties (e.g., xanthan gum aggregates, or emulsion oil droplets), and it is this structure that is reflected in the flow curve yield value. Interactions at a molecular level have shorter relaxation times and are of interest, since they also contribute to gel structure. In this evaluation, a pulse shearometer may be used. This instrument gives an indication of true elasticity, the "shear" modulus (or "gel modulus" or "elastic modulus"). The velocity of a 200 Hz shear wave transmitted through the sample is measured, and from this is calculated the shear modulus. A fuller description is given by H. S. Ellis and S. G. Ring, "A Study of Some Factors Influencing Amylose Gelation," *Carbohydrate Polymers*, 5, pp. 201–213 (1985).

Two materials have become recognized for outstanding texture building properties and dispersion stabilization. One is xanthan gum, a very high molecular weight polymer (microbial source) that forms aggregates. Its structure apparently results from these aggregates and generally from molecular entanglement. A very high degree of shear thinning results and very high apparent viscosity is observed at low shear rates. The second material is microcrystalline cellulose (MCC), such as Avicel ®, where a colloidal sized elongated crystal provides structure that appears not to involve molecular engagement, but rather a "house of cards" structure. Here colloidal forces maintain the crystals in a certain formation with respect to each other and with respect to the other components of the food matrix.

Most foods are either emulsions or dispersions. Consequently, portions of those macromolecules used as "thickeners" usually absorb to the surface of the disperse phase material and thereby help stabilize the suspension. This absorbed layer gives added textural enhancement by providing a link between the solubilized species and the dispersed material. Associated with texture is flavor or taste. Thinning, i.e., viscosity reduction, that occurs in the mouth is not only desirable from strictly rheological considerations, but also for flavor since a sensation of flavor release results from thinning, (Sanderson, *Gums and Stabilizers for the Food Industry*, Pergamon (1982)). This thinning may derive from increased shear in the mouth that occurs during mastication. Thus, there is thinning as a result of inherent shear thinning, which becomes more apparent as mastication proceeds. For foods served at temperatures lower than that of the mouth there is the thinning effect from the normal dependence of viscosity on temperature.

Another form of stabilization is retardation of ice crystal growth in the frozen state as a result of high viscosity and/or physical barrier. Growth of ice crystals results in loss of smoothness and damage through freeze dehydration. Hydrocolloids (gums) are used in foods for texture improvement via viscosity, yield stress and shear thinning modification, stability via emulsification and structure, and flavor release via shear thinning.

Such considerations also attend the preparation of pharmaceutical. While a principal concern for the manufacture of pharmaceutical is the effectiveness of the medicaments contained therein, aesthetic considerations are also significant. Thus, the manufacturers of pharmaceutical, both ethical and over-the-counter, are much concerned with rheological and other physicochemical properties of those pharmaceutical. Improvements in those properties, as well as improvement in the stability of the medicaments contained therein, are principal concerns of the pharmaceutical industry. Improved rheological properties of pharmaceutical through improved carrying systems are also desired, as are improvements in exipiency. Such improvements are much desired and long sought after.

Prior to the present invention, a variety of methods were described and claimed in the patent literature for processing, and/or modifying plant matter and its recover and use in food and drug products. For example, U.S. Pat. No. 3,023,104, which issued on Feb. 27, 1962 to O. A. Baltista, discloses and claims a reduced calorie food composition containing cellulose crystallite aggregates. The aggregates are obtained by an acid hydrolysis and mechanical disintegration of natural fibers such as ramie, cotton, bleached sulfite pulp, bleached sulfate wood pulp and the like.

A food supplement from vegetable pulp is disclosed in U.S. Pat. No. 4,241,093, which issued Dec. 23, 1980 to S. A. Farag et al. A bland, free-flowing food supplement was obtained from water-extracted vegetable pulp such as sugar beets, apples, corn, peas, turnips, and the like. The pulp was then bleached and provided a food supplement containing curde fiber, curde protein and a major amount of nitrogen-free extracts.

U.S. Pat. No. 4,307,121, which issued Dec. 22, 1981, disclosed and claims a process for providing a cellulosic product for human consumption from certain agricultural foodstuff by-production. Materials such as ground soy hulls, yellow field pic hulls, corn bran and ingor beets are subjected to multiple oxidation conditions with chlorine gas and, thereafter, separating some short fiber cellulose.

Food products containing microfibrillated cellulose are disclosed in U.S. Pat. No. 4,341,807, which issued July 27, 1982, to A. F. Turbak et al. The products are obtained by mixing together an edible liquid, a food flowing additive and fibrous cellulose, and then repeatedly passing the mixture through a high pressure homogenizer under conditions wherein the cellulose is converted to microfibrillated cellulose. The homogenizer has a small diameter orifice, and the mixture is subjected to a high pressure drop and a high velocity shearing action followed by a high velocity decebrating impact against a solid surface.

A method for mechanically processing thermochemically pulped wood, whereby the wood fibers are further transformed into smaller fibrils generating a highly "beaten" pulp, is described in U.S. Pat. No. 4,373,702 "Microfibrillated Cellulose" by Turbak et al. The technique described in this patent employs repeated impact discharge against a solid surface at high pressures, (greater than 3000 psi), of a liquid suspension of fibrous cellulose using commercially available homogenization equipment. The resulting product displays unusual properties of high viscosity and gel structure not previously known for high "beaten" or mechanically "diminuted" wood pulps.

Edible suspensions containing microfibrillated cellulose are disclosed by A. F. Turbak et al in U.S. Pat. No. 4,378,381, which issued Mar. 29, 1983. It is indicated that the microfibrillated cellulose is a new type of cellulose, which is distinguished from prior cellulose by vastly increased surface area, greater liquid absorption characteristics and greater reactivity.

A process for preparing a cellulosic product for human consumption is disclosed in U.S. Pat. No. 4,486,459, which issued on Dec. 4, 1984 to J. B. Thompson. The process produces purified short fibers of cellulose from the hulls of edible legumes by solubilizing non-cellulosic material with an oxidying agent, separating a cellulose pulp, further oxidation and finally, heating in the presence of a base.

In G.B. No. 2,089,640, a method is disclosed for making an animal feed from the liquid fraction of an acid hydrolyzed beet pulp. The reaction time and acid concentration of the disclosed method cause severe degradation and hydrolysis of the hemicellulose complex to constitutive uranic acids, pentoses and hexoses which are desired for an animal feed product application. Because of the lack of high shear during hydrolysis and discharge to atmospheric pressure, the membranous structure of the sugar beet parenchymal cell tissue is not highly dispersed and demonstrates a fiber-like behavior.

OBJECTS OF THE INVENTION

It is a principal object of this invention to provide improvements in the rheological properties of comestibles including foods and drugs.

It is a further object of this invention to prepare such comestibles through the admixture of parenchymal cell cellulose thereto in order to secure improved physical or physicochemical properties for such materials.

A further object is to provide a source of non-nutritive or dietary fiber for use in comestibles. A further object is to improve the viscosity, stabilization, and texture of foods and drugs and comestibles in general.

A further object is to provide methods for the preparation of comestibles with the inclusion of parenchymal cell cellulose in order to provide improved physical and physicochemical properties thereto.

A further object is to provide foodstuffs having lower levels of fat, cholesterol, or other fatty substances while retaining acceptable physical and physicochemical properties appropriate to the food.

Yet another object is to provide foodstuffs having overall lower caloric value, while retaining good physical and physicochemical properties, good taste, and suitable processability.

Another object is to provide improved pharmaceutical excipients.

Still other objects will become apparent to persons of ordinary skill in the art from a review of the present and appended claims.

SUMMARY OF THE INVENTION

It has now been discovered that the addition of parenchymal cell cellulose to foodstuffs, drugs, and other comestibles, can improve the physical, physicochemical and stability properties of such materials. It has also been found possible to provide methods for preparation of foods and drugs through the incorporation of parenchymal cell cellulose (PCC) therein, to result in unique compositions having improved properties. Thus, it has been found possible to prepare a stabilized dispersion of a first material in a second material comprising an amount sufficient to stabilize the dispersion of parenchymal cell cellulose. Such dispersions may comprise liquid-in-liquid emulsions, oil-in-water emulsions, water-in-oil emulsions, foams of gas and liquid, emulsions or suspensions of solid and liquid, dispersions of gas with a plurality of liquids, and other multi-phase systems. Such materials find particular utility in the food and drug industries, as well as in other industries dealing with comestibles.

BRIEF DESCRIPTION OF THE DRAWINGS

FIGS. 6 and 7 are graphs depicting the shear training ability of PCC, xanthan gum and Avicel ®.

DETAILED DESCRIPTION OF THE INVENTION

Figure 1:
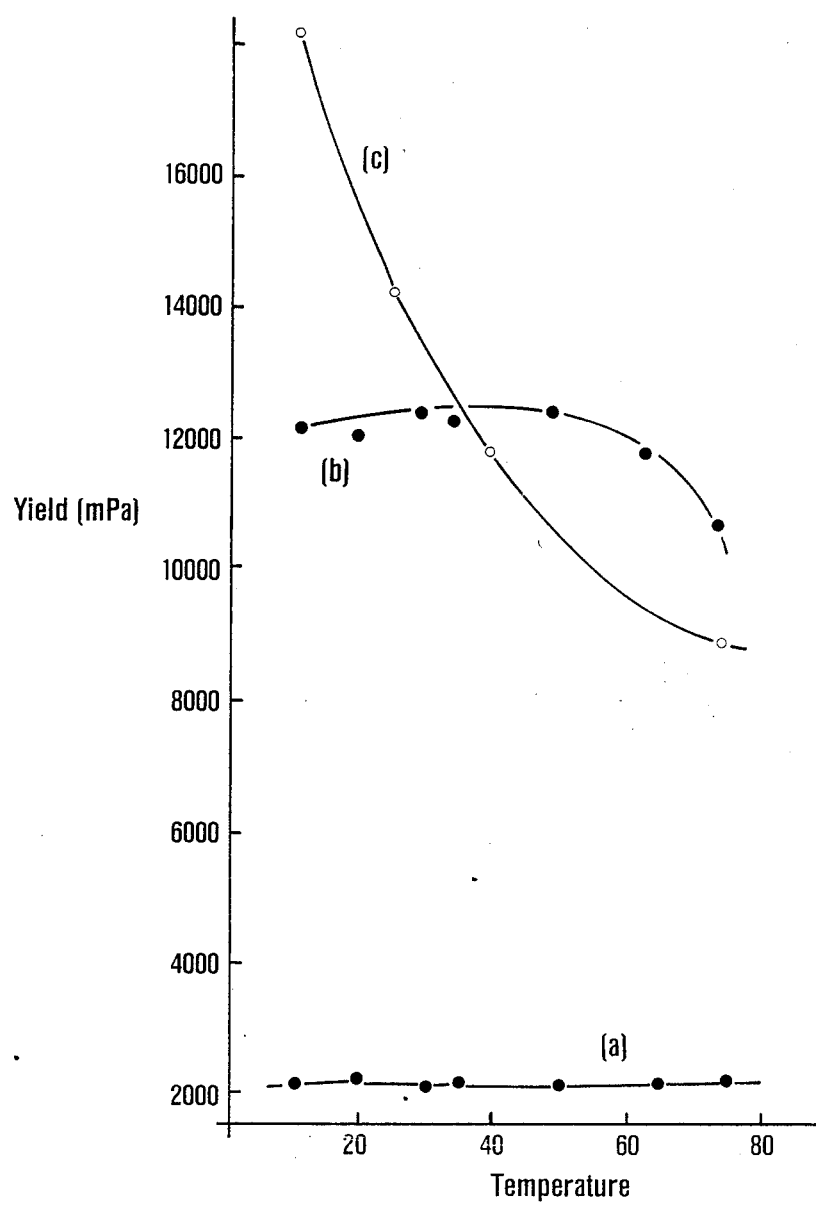
FIG. 1 is a graph depicting yield values as a function of temperature for PCC, xanthan gum and Avicel ®.

In accordance with one embodiment of the present invention, comestibles are provided comprising parenchymal cell cellulose. Parenchymal cell cellulose, as herein defined, has been found to be extraordinarily useful in a number of aspects of comestible production. PCC is highly utilitarian for a wide variety of rheological uses and improvements. Such comestibles may be prepared in the form of emulsions, dispersions, foams, gels, doughs, and other forms. In this regard, the term "dispersion", as employed throughout the specification and appended claims, is defined generically to include emulsions, foams, gels, doughs, and the like.

All foods are dispersions containing a least one component dispersed within another, the former being referred to as the "disperse phase," the latter as the "continuous phase." Even drinking water falls within this definition as a result of the presence of particles of colloidal size (page 1 in *Colloids in Foods,* E. Dickinson and G. Stainsby, Applied Science Publishers, London and New York (1982). In a similar fashion, liquid honey will also contain particles that are of colloidal size. Sugar on the other hand, according to this definition, would be classed as a food additive. While it may be considered that there is no practical or logical justification for distinguishing between foods and food additives, this distinction is nevertheless made (page 70 in *Food and Emulsions,* ed. S. Frisberg, Marcel Dekker, Inc., New York and Basel, 1976). Thus, a food is a dispersion that is also a comestible. In the realm of formulated foods, the definition as a dispersion is absolutely essential to the food scientist. Not to recognize foods as dispersions overlooks one of their fundamental properties—that which defines them as being thermodynamically unstable and, therefore, requiring the determination of "shelf-life."

It is the disperse nature of foods that gives to them one of their most important properties, that referred to as "texture." Thus, the "yield" (the yielding of the food as one "bites into it"), the shear thinning (such as salad dressings that look thick in the bottle, but seem quite liquid as they flow down the throat), and flavor release from shear thinning are all important results from foods being dispersions, (Pettie, in *Polysaccharides in Foods*), Butterworths, 1979; Sanderson, Prog. Fd. Nutr. Sci 6 (1982) 77–87; Sanderson, in *Gums and Stabilizers for the Food Industry,* Pergamon, 1982; Sherman, same volume).

Foods are usefully categorized into certain functional divisions. However, there is no one system that is recognized as definitive for all concerned. Thus, a marketing person may use categories that are different from those used by the food scientist.

For food technologists and scientists, and often also for marketing or other people concerned with foods, a useful classification, and one used throughout this specification and appended claims, is the following:
(i) food emulsions,
(ii) food foams,
(iii) food batters,
(iv) food doughs, and
(v) other food dispersions.

An emulsions will be further defined as a dispersion which is either an oil (or fat)-in-water or water-in-oil (or fat) emulsion [in most cases herein the use of the term "water" may more appropriately be replaced by "aqueous" thus, indicating that other materials may be dissolved/dispersed therein]. Thus, either the oil (fat), or the aqueous part, may be the disperse phase. Cream, an oil-in-water emulsion, when churned, inverts to become butter which is a water-in-oil emulsion.

A foam is a dispersion of gas particles embedded in a matrix, which in turn will also be a dispersion, either of solids in liquid, solids in solids, or an emulsion.

While cake batters are also distinguishable as cake "emulsions" (I. S. Shepherd and R. W. Yoell, in *Food Emulsions* ed. S. Friberg Marcel Dekker Inc., 1976), it is usually better to define them under "batters" to make a distinction from doughs, the latter having a more viscous texture than the former. [A batter may normally be manually stirred with a spoon, or mechanically mixed with beaters, whereas a dough is manually mixed by kneading or mechanically mixed with dough hooks.] A dough is also often a food emulsion, if a fat such as shortening has been used as part of the formulation; however, some doughs may be made up only of flour and water, with possibly a leavening agent—thus, the useful distinction of a separate category as dough. Thus, a batter is a pourable dispersion in which the disperse phase is composed of various materials often including an oil (fat), protein aggregate, milk solids, starch, spices, and other additives such as fruit pieces, or nuts.

A dough is a moldable dispersion which is too elastic to be considered pourable in the conventional sense (i.e., it takes a comparatively long time to "pour" a dough, and stretching is a more appropriate term than flowing to describe its motion during such "pouring"). The disperse phase of a dough usually includes a starch; it may also include protein aggregates, oil (fat) emulsion particles, milk solids, spices, and other additives such as fruit pieces or nuts. The disperse phase of a dough normally forms a higher percentage of the total recipe than it does in a batter—hence, the more solid-like behavior.

While emulsions, foams, batters and doughs certainly constitute most formulated foods, and in the absence of rigid definitions most natural foods as well, it is obvious that there are foods that do not easily fall into any of these subdivisions and, therefore, "other food dispersions" must be another category. However, it is neither practical, nor is the number of them sufficiently large, to further subdivide this section at this level of definition, without also further subdividing the other categories, as named, as well.

Comestibles in accordance with the present invention may be prepared comprising yolk-containing aqueous emulsions, frozen confections, ice creams, ice milks, frozen toppings, mayonnaise, mayonnaise substitutes, thixotropic condiments, sauces, and a wide variety of other materials. Such comestibles may also be prepared comprising jellies, whips, and a whole host of dispersions, emulsions, gels, foams and other materials useful in the food and drug industries. The present invention also provides reconstitutable mixes for preparation of any of the foregoing materials.

A particular, preferred embodiment of the present invention provides comestibles in the form of foams such as albuminous foams, proteinaceous foams, frozen foams, whipped toppings, and a whole host of reconstitutable mixes for such materials and replacements and substitutes therefore. In accordance with yet another embodiment, parenchymal cell cellulose may be incorporated into batters, doughs, mixes, and the like, in order to improve texture, processability, or other rheological properties.

Another preferred embodiment secures improvements in beverages and the like though the addition of PCC thereto. Juices, dairy and non-dairy frozen beverages, concentrates and the like can all benefit.

In accordance with another preferred embodiment, methods for altering a physical or processing property of a comestible are provided comprising an addition to the comestible of an amount sufficient for effecting the alteration by parenchymal cell cellulose. In accordance with other preferred embodiments, the amount of parenchymal cell cellulose added to the material to effect the alteration is between about 0.01 and about 30% by weight. It is still more preferred to add from about 0.1 to about 5% by weight.

Dietetic or other specialty comestibles may also be prepared in accordance with this invention in view of the fact that parenchymal cell cellulose has a negligible food value and is devoid of fat or cholesterol. Thus, methods for preparing comestibles having reduced caloric content while maintaining commercially acceptable physical and processing characteristics are comprehended by this invention comprising formulating the comestible to include, for example, at least about 0.2% by weight of parenchymal cell cellulose. Similar improvements in the preparation of comestibles to provide such comestibles having reduced lipoprotein or fat levels while maintaining commercially acceptable physical and processing characteristics are also included within the invention. Thus, such comestibles are preferably formulated to include at least about 0.2% by weight of parenchymal cell cellulose.

A number of aging processes in foods derive from migration of molecules within the food product so that local high concentrations occur. If these molecules prefer a crystalline arrangement, then nucleation may occur with subsequent crystal growth often to unacceptable size. For example, in most frozen foods, water forms ice crystals that grow with time, the larger crystals growing at the expense of the smaller crystals: in ice cream this results in the perception of granularity and a loss of creaminess in texture. Another result of ice crystal growth is "freeze dehydration" as water is "robbed" from the non-aqueous components of the product. The freeze dehydration produces changes to the higher levels of structure of polymeric molecules such as proteins and carbohydrates that are present: undesirable textural changes such as toughness in meats result. Considerable efforts in food research go toward finding methods to prevent ice crystal formation, i.e, to promote freezer storage stability. Another similar process is the recrystallization of starch molecules that results in staling of bread and structural changes in starch gels: this occurs at non-refrigerated storage temperatures. Similarly, sugar forms crystals: this is often noticeable in frozen products, particularly for those where sugar level is relatively high, such as butter tarts.

One embodiment of this invention is the discovery that PCC impedes the development of the above ageing processes so that ice cream creaminess is prolonged during storage, and bread maintains a fresh elastic loaf texture for longer periods of time. To achieve such prolonged storage stability improvement, comestibles are preferable formulated to include at least about 0.01% by weight of parenchymal cell cellulose.

In accordance with certain embodiments of the present invention, more complex mixtures may be added to, or included in the foods, drugs and cosmetics of the present invention in order to improve them. Thus, parenchymal cell cellulose may be co-isolated with certain hemicellulosic components of the materials from which the PCC is derived. Thus, sugar beet pulp, citrus pulp or other parenchymal cell containing material may be treated in such a way as to co-isolate both parenchymal cell cellulose and certain hemicellulosic components of those plant materials. The resulting, combined materials may be useful for any of the methods, and in any of the materials discussed above under appropriate circumstances. Thus, the hemicellulosic components of such blends, mixtures or co-isolates form a natural gum having properties not unlike naturally-occurring gums well known to persons of ordinary skill in the food science art. Accordingly, the inclusion of the hemicellulosic components may find beneficial use in one, or more, embodiments of the present invention.

The cell walls of parenchymal cells, especially parenchymal cells found in sugar beets and citrus, possess unique morphologies. A method for the isolation of such cells from non-parenchymal cellulosic and other structures of sugar beet pulp, or other parenchymal cell sources, has been discovered and is disclosed in U.S. Ser. No. 512,940, filed July 12, 1983, incorporated herein by reference, or in EPO Patent No. 102,829, incorporated herein by reference. Moreover, dispersions and suspensions of such cellulosic components of parenchymal cells have been made and have been found to possess unique rheological, chemical and physical behaviors and properties useful for the practice of certain embodiments of this invention.

An understanding of the structural organization of cellulose-based articles is helpful to an understanding of the present invention. It will be appreciated to those skilled in the art that numerous systems have been used to describe cellulosic infrastructure in the past. The present organizational tableau has been developed in order to focus attention upon the differences among various materials comprising cellulose.

Cellulose is known to comprise a linear array of Beta 1-4 D-glucopyranose units. With regard to this primary form, all celluloses are the same. Thus, starch and dextran, which are also glucose homopolymers, differ at this level of analysis.

The arrangements of chains of Beta 1-4 D-glucose to form an ensemble comprises secondary structure of cellulose. In native forms of cellulose, the ensemble is designated the microfibril. Thus, the chains within the ensemble may be arrayed in parallel, anti-parallel, or complex structures; they could also be arranged in a random fashion. It is at this secondary level of structure that elementary cellulose types have been recognized by those skilled in the art. Representative of the structure observed at this level are cellulose I, II, III and IV, which comprise the known forms of crystalline cellulose. Low order chain arrangement, which may be more or less random depending on the pedigree of the cellulose, comprises amorphous cellulose. Native forms of cellulose contain type I structured regions, while reconstituted celluloses such as rayon are largely type II. The dimensions of native, individual microfibrils are largely a function of the number of parallel chains generated by the biosynthetic organelle characteristic of the specific cell or tissue being assembled.

The microfibril comprising the secondary structure of cellulose may in turn be arranged to form a tertiary structure. Thus, regions of varying crystallinity may be dispersed inter se or among areas of amorphous cellulose in adjacent microfibrils to form strong intermicrofibril associations which stabilize varying tertiary structures. Accordingly, structures such as fibrils, bundles, sheets and the like, may be seen to comprise tertiary structures. The cell wall of a parenchymal cell is best described as a tertiary structure. In this regard, such a parenchymal cell wall of a sugar beet is easily distinguished from, for example, a stalk fibril or fiber, which may also be found in sugar beets.

The macro structure of a cellulosic material is best understood as being an arrangement or combination of tertiary structures. Thus, the plant vascular bundle known as phloem may be distinguished from a similar vascular bundle, xylem, as having a different quaternary structure even though the tertiary structures may be similar or even identical. Similarly, parenchymal cell walls (tertiary structures) may be constructed somewhat differently to form the parenchymal cells of, for example, sugar beets or certain fruits. Quaternary structure may also be envisioned as comprising macroscopic assemblages characteristic of specific plant tissues. Such structures will, of course, comprise non-cellulosic materials as well.

In view of the foregoing, it will be appreciated that the structure represented by the isolated cell walls of parenchymal cells such as those found in sugar beets and other pulpy plant tissue is distinct in kind from the various other secondary and tertiary structures known to those skilled in the art. It has now been found that such cellulose derived from cell walls of parenchymal cell cellulose or PCC, has unique physical, chemical and rheological properties. Moreover, dispersions of such parenchymal cell cellulose, especially in aqueous media, have other useful physical and rheological properties as well. It is believed that isolation of parenchymal cell cellulose has not heretofore been accomplished and that such cellulose and cellulosic dispersions have not heretofore been known.

The physicochemical and functional uniqueness of PCC is thought to be related to its secondary and tertiary structure. Primary structure, the way in which the D-glucose molecules are combined to form a linear polymer, is the same for all cellulose. The primary structure chains have high affinity for each other and spontaneously self-associate to form amorphous or other levels of structure which reflect their ordered grouping and spatial arrangement with respect to each other. It is here that PCC begins to significantly differ from most other forms of cellulose. The assembly of the microfibril is controlled by the biosynthetic organelle(s) to be characteristic of the physiological obligations of the cell being formed. Low angle x-ray crystallography now indicates that the PCC is composed of order regions of very small dimension with few reflecting planes. The shape associated with secondary structural elements of PCC now appears from high resolution, transmission electron microscopy to be a microfibril structure of extremely small dimensional order. In summary, the membrane morphology of PCC reflects a tertiary structure resulting from intermeshed layers of microfibrils.

Finally, structural specialization forming the basis of functional plant tissue is reflected by quaternary structure whereby the tertiary structural elements are combined with other macromolecular substances such as hemicelluloses, lignins, proteins, etc. Parenchymal cell cellulose is prepared primarily from structural manipulation at the quaternary and tertiary level, although some effect on lower levels of structure would be expected. In contrast, production of other highly functional celluloses such as microfibrillated cellulose and microcrystalline cellulose from high purity alpha cellulose wood pulps reflects structural manipulation at the tertiary and secondary levels, respectively. Thus, each is distinguished from PCC.

A further distinction between PCC employed in the present invention, and the microfibrillated cellulose or microcrystalline cellulose of the prior art, is readily evident from an examination of the source of the starting materials.

Wood cellulose is usually present in the form of a fiber or thread-like structure and is a long, slender thick-walled cell, or sclerenchyma. Sclerenchyma exists in higher plants and is composed of cells having cell walls which have thickened and become liquified. Such cells are usually without nucleous or protoplasm and are incapable of further growth when mature.

In contrast, parenchyma cell cellulose is a dispersed membranous product derived from the cell walls of parenchymatous tissues. Such tissue is composed of living, thin-walled cells, which make up the bulk of the pulp of fruits, the pith of stems and the like.

According to one embodiment, PCC can be isolated from the acid hydrolysis of sugar beet pulp at pH's below about 4.5 and preferably at pH's below about 4.0 and even more preferable between 4.0 and 2.0. This condition of strong acidity is maintained at a temperature above room temperature, and for a period of time which is sufficient substantially to liberate pectin and arabinogalactan from the sugar beet pulp.

It is preferred that a temperature greater than about 125° C. to about 250° C. and even more preferred to employ temperatures between about 140° C. and about 200° C. Still other preferred embodiments employ temperatures between about 150° C. and 180° C.

As will be appreciated by those skilled in the art, the reaction times which are sufficient to liberate hemi-cellulosic components from parenchymous tissue, pectins and arabinogalactans, will vary depending on the pH employed and the reaction temperature. It is preferred that reaction times less than about 600 seconds be employed. It is still more preferred that reaction times less than about 360 seconds be so employed with a still more preferred range being reaction times below about 200 seconds. In general, reaction times effective to liberate the components will be greater than about 15 seconds and preferably greater than about 30 seconds. According to one preferred method for the isolation of PCC, sugar beet pulp in aqueous slurry is acidified to a pH of about 2.5, with concentrated hydrochloric acid and hydrolyzed for approximately 120 seconds at 160° C. In accordance with another approach, unlimed citrus pulp was acidified to a pH of about 2.2 with HCl and hydrolyzed for about 170 seconds at about 165° C. As will also be understood by those skilled in the art, wide combination of pH's, reaction time and temperature will be satisfactory for obtaining PCC.

Those skilled in the art will appreciate that it is best to define the reaction conditions for preparing PCC by what they accomplish rather than by their numerical values. Thus, a sufficient combination of pH, reaction time and reaction temperature which allows the liberation of pectin and arabinogalactan from spent sugar beet pulp (or other parenchymal cell containing plant material) without the substantial degradation thereof is desired. In this context, substantial degradation refers to degradation in excess of approximately 25% of the total mass of either pectic or araginogalactan component. For certain preferred embodiments, it is preferred that such degradation be minimized. For others, a certain degree of degradation may be allowed, or even encouraged, such as when coproduction of novel vegetable gums with PCC is desired. It is believed that from analysis of the foregoing discussion concerning reaction conditions, one of ordinary skill in the art will readily be able to appreciate those modifications which must be made in the combination of pH, reaction time and reaction temperature to allow the coproduction of hemicellulosic components, for example, sugar beet pulp, for any particular purpose.

The isolation of PCC from sugar beet pulp or other parenchymal cell-containing plant material may also be accomplished in strongly alkaline conditions. Thus, combinations of high (strongly basic) pH, relatively high temperature and relatively short reaction times may be so employed for such isolation. This combination of strongly alkaline pH at high temperatures for short times can allow the coproduction of hemicellulosic components from such plant materials without substantial degradation if such is desired. In some applications, the co-isolation of PCC with hemicelluloses may be desired. In this regard, it is preferred that pH's greater than about 8.0 be employed for this hydrolysis. It is still more preferred to employ pH's between about 9.0 and about 13, and even more preferred to employ pH's from about 10.5 to about 12.

Combinations of pH, time and temperature may be varied by those skilled in the art while not departing from the spirit of this invention. Such persons will appreciate that variations of such parameters may be employed to modify the total output of hemicellulosic materials to be produced in accordance with this invention and that diverse vegetable gums may be formulated thereby. In accordance with the practice of certain embodiments this invention employing alkaline hydrolysis, conditions of time and temperature are employed which are substantially sufficient to isolate the hemicellulosic component without substantial degradation thereof. In this regard, those skilled in the art will appreciate that the hemicellulosic component present as pectin will be quickly hydrolyzed under basic conditions to salts of pectin acids. Such pectinic acid materials can comprise useful vegetable gums and other materials which in combination with PCC can lead to commercially desirable combinations.

The times and temperatures which are useful for the alkaline hydrolysis in accordance with the present invention are similar to those which are useful for the acid hydrolysis. Thus, temperatures between about 125° C. and 250° C. may be employed. It is preferred that temperatures between 140° C. and about 200° C. be employed, while still more preferred are temperatures between about 150° C. and 180° C. Reaction times less than about 600 seconds are preferred with reaction times less than about 200 seconds being more preferred and reaction times from about 30 to about 200 seconds are still more preferred for certain embodiments. In general, reaction times greater than about 15 seconds are needed.

The acid or basic hydrolysis of sugar beet pulp, or other parenchymal cell-containing materials to isolate PCC or hemicellulosic components is greatly facilitated by the employment of physical shearing in connection herewith. It is preferred that hydrolysis be conducted in conjunction with physical shearing to maximize the fibrillation of PCC. In this regard, it is believed that the physical stressing or shearing assists in the disruption of the intracellular organization of parenchymous tissue and facilitates the liberation of hemicelluloses. A wide variety of apparatus may be employed to effect such physical shear. Thus, in accordance with the preferred embodiment, a tubular reactor is employed which passes a slurry of parenchymal cell containing material at elevated temperature and pressure and at the desired pH through its length to one or more exit orifices. The slurry is then sprayed or "shot" through the orifice into a region of lesser pressure. This technique, which is well known to those skilled in the art in terms of flash evaporation and other processes, provides a source of mechanical shear which is well suited to the practice of the present invention.

Other forms of mechanical shearing may also be employed after isolation of parenchymal cell cellulose or directly upon the reactor discharge. With certain embodiments, shearing may be accomplished through ultrasonics, impact discharge or through any other technique which serves to effect substantial disruptions of the cellular organization and induce fibrillation of the membranes.

It is most convenient to employ physical shearing simultaneously, or shortly subsequent to the hydrolysis of sugar beet pulp or other plant material. Thus, the tubular reactor with "blow down" exit orifice is greatly preferred due to consideration of convenience and cost. It is also possible, however, to employ hydrolysis and physical shearing in separate steps. Thus, the plant material may be hydrolyzed under conditions of pH, time and temperature as hereinabove described, and stored under nonhydrolytic conditions prior to, for example, batchwise physical shearing in a high shear device. Other modifications of the hydrolysis/physical shearing scheme will also be apparent to those skilled in the art.

The foregoing hydrolysis coupled with physical shearing also serves to liberate parenchymal cell cellulose from parenchymal cell-containing plant material, especially sugar beet and citrus pulp. It is believed that the various forms of bonding between the parenchymal cell walls comprising parenchymal cell cellulose and other forms of cellulose in spent sugar beet pulp or other plant material is disrupted through the combination of hydrolysis and physical shearing.

A preferred reactor useful for the acid or basic hydrolysis in accordance with one or more embodiments of the present invention comprises a tubular design. Thus, twelve stainless steel or other tubes having approximately ½ inch inside diameter are parallel mounted through a 25 foot length of 12 inch inside diameter pipe and connected in series. Means are provided for introducing steam or other heating source into the outer jacket of the reactor in a controlled fashion so as to provide the desired temperature in the reaction tubes. An input pumping means is also provided for feeding a stream of pH adjusted plant material slurry into the reactor tubes. The exit end of each reactor tube is provided with an adjustable orifice of small cross-sectional dimension. The orifice serves a dual purpose of maintaining internal pressure within the reactor tubes, and or providing exit velocities which generate high mechanical shearing effects on the exit product stream when the same is forced therethrough.

In typical hydrolytic reactions in accordance with this invention, pulp is fed to the foregoing tubular reactor at head pressures ranging from about 200 to about 2000 pounds per square inch. Superficial linear velocities at the exit orifice have been estimated from about 10 to 100 meters per second. Thus, strong shear forces are encountered at the orifices. The product of the reactor is effectively "flashed" to atmospheric pressure after exit from the orifices and passed to subsequent processing operations.

While numerous reaction protocols may be employed by those skilled in the art for the practice of one or more embodiments of the present invention, in general, a slurry of plant material such as spent sugar beet pulp suspended in aqueous medium is adjusted to the desired pH, either strongly acid, or strongly alkaline, and passes through a suitable reaction apparatus such as foregoing tubular reactor. The pH modified slurry is subjected to combinations of temperature and time at a pressure generally above atmospheric pressure. The material is then, in accordance with the preferred embodiment, passed through an exit orifice to atmospheric pressure to effect physical shearing.

The resulting material may be viewed as having solid and liquid components. Separation of the solid and liquid material is generally followed by further processing. The solid material may be viewed as crude parenchymal cell cellulose mixed with other cellulosic debris such as vascular bundles, fiber and the like. Additionally, other solid components may be present. It is preferred that the crude parenchymal cell cellulose be bleached, or otherwise rendered more suited to dispersion by contact with a bleaching medium such as hypochlorite, peroxide, or other material. The bleaching step may, in some instances, facilitate mechanical classification and subsequent isolation of substantially pure parenchymal cell cellulose from non-parenchymal cell residuum.

Concentrates or isolates of parenchymal cell cellulose display several unique properties. A low-solid slurry of PCC, such as about 0.5% to 2% by weight in water, forms a stable homogeneous suspension following high shear homogenization. It is believed that high shear partially fibrillates the membrane structure causing distention and dislocation of microfibrils from the surface, thereby creating an "expanded" or "hairy" membrane assemblage of microfibrils. This suspension posses a beneficial rheology, probably due to physical entanglement and interparticle association of the platelet-like form of the fibrillated PCC, thus obtained. Thus, fibrillated PCC suspensions have high resting viscosities and possess thixotropic and pseudoplastic characteristics. The solution rheology of a PCC dispersion is pseudoplastic and is characteristic of a hydrocolloid suspension. It is believed that the expanded microplatelet structure of PCC is responsible for the unique solution rheology of the dispersed preparation. The highly hydrated platelets can be made similar in density to water and to form gravitationally stable suspensions. The gross shape of hydrated PCC is that of an elongated ellipsoid, although there is considerable heterogeneity of shapes. The average major dimension of the isolated membrane is 20 to 100 microns with a membrane thickness of several hundred angstroms. In the moderate imposed shear range (10 to 100 sec$^{-1}$), PCC viscosity behavior can be approximated by the Bingham plastic model used commonly for characterizing colloidal suspensions or the power law. The mild thixotropic behavior exhibited by PCC results from time dependent translational relaxation to form a gel structure or hydrodynamic alignment upon standing or mixing, respectively. The platelet-like membranes are extremely durable to shear and are not affected by extremes of temperature, salts of pH. At PCC concentrations in excess of 2% w/w, interparticle interaction begins to dominate factors influencing the solution rheology and the viscosity rapidly increases. At 4% w/w concentrations, PCC can form a zerogel.

The cellulose isolated from citrus pulp is somewhat different than that obtained from the sugar beet. While citrus PCC morphology is predominantly membranous, there is considerable heterogeneity of size; the majority of the particles cannot be sprayed through a 100 mesh screen. This is in contrast to PCC from sugar beets which has a relatively uniform particle size, and, aside from the fiber fraction, is easily rinsed through a 100 mesh screen. The citrus pulp cellulose is a film former like PCC and displays a similar homogenate rheology.

In the absence of water, the membrane micro-platelets strongly associate by hydrogen bonding. The inter-membrane interaction is unusually effective upon drying due to high surface area to volume ratio of the fibrillated platelet structure. Depending on the amount and efficiency of hydrogen bonding interaction, dried PCC films may be extremely difficult to rehydrate. Incorporation of a chaotropic agent such as certain cellulose ethers has been found useful in preparing easily rehydratable PCC.

Various uses for PCC in food products have now been demonstrated. In the examples provided in this study, PCC has been used at very low levels to replace such higher levels of various functional components of several different food products (e.g., the oil phase/emulsifier of mayonnaise, fat in whipping cream, egg/flour in cakes, starch in cooked puddings). In most cases, the control recipe has been severely stressed over that of the normal recipe, e.g., by partially replacing egg white with water, by partially replacing the whipping cream fat with water, etc.: the addition of PCC has demonstrated excellent functionalities important in foods. PCC has also been used to demonstrate remarkable stabilizing and texture building properties in model emulsions, meringues and ice creams.

The PCC material is an excellent texture building agent and emulsion stabilizer. At equal concentration, it demonstrates higher yield and viscosity than either micro-crystalline cellulose or xanthan gum, and is more thinning with increasing temperature than is xanthan. Rheological data indicate greatly superior properties to both microcrystalline cellulose and xanthan gum for texture and stabilization purposes. PCC combines both the colloidal particle type of gelation characteristic of micro-crystalline cellulose with the polymeric cross-linked type of gelation characteristic of xanthan gum.

In accordance with one or more embodiments of the present invention, parenchymal cell cellulose can be added to comestibles including foods, drugs and cosmetics in varying amounts for varying purposes. In general, however, amounts of parenchymal cell cellulose between about 0.01% and about 10% by weight of the total has been found to be useful. It is more preferred that amounts of parenchymal cell cellulose between about 0.02% and about 5% by weight be included with amounts between about 0.01% and 2% being still more preferred. Persons of ordinary skill in the art will appreciate that varying amounts of PCC will be appropriate for varying functional uses. Thus, for the stabilization of an oil-in-water emulsion, such as the improvement of artificial mayonnaise ice creams, certain thixotropic condiments and the like can benefit from inclusion of from about 0.01% and about 10% of PCC by weight of the total. Even more preferred is the inclusion of from between about 0.02% and about 5% of PCC in such materials with additions between about 0.1% and about 2% by weight being still more preferred. Similar considerations attend the consideration of improved water-in-oil emulsions where amounts of parenchymal cell cellulose between about 0.05% and about 20% by weight, still more preferably between about 0.1% and 10% by weight and even more preferred between about 0.2% and 5% by weight can be used. Such water-in-oil emulsions include certain condiments, spreads and the like. Pharmaceuticals having these kinds of emulsions benefit from similar treatments and they employ generally similar amounts of parenchymal cell cellulose for their improvement.

The improvement of comestible foams or froths such as air-in-liquid (e.g., whipping cream, whipping cream substitutes and other whipped materials) can benefit from the inclusion of PCC therein. Thus, amounts between about 0.01% and 10% by weight are preferably used. Even more preferred are amounts between about 0.02% and 5% by weight with addition of between about 0.5% and about 2% by weight being still more preferred. Once again, some drugs having such form may benefit from the practice of this embodiment of the invention.

PCC stabilizes frozen foods such as meat and fish resulting in improved cooked quality and storage stability. The suspending power of PCC shows utility in concentrated juice, jams, sauces and the like by suspending pulp components and improving texture. Amounts of from abut 0.01% to about 5% are useful generally.

In accordance with yet another embodiment, parenchymal cell cellulose is added to batters, doughs and other bakeable material. In such cases, parenchymal cell cellulose improves the structure, body and physical properties of such batters or doughs lending stabilization and improved viscous behavior while imparting very little nutritive value and at a low cost. Amounts of PCC between about 0.01% and about 10% may be added with amounts between about 0.05% and about 2% being still more preferred. In general, parenchymal cell cellulose may be added to foods and drugs in many forms and formulations. Thus, it may be added to improve the qualities of gels, sols, aerosols, foams, emulsions and, generically, dispersions of all types. The exemplary material which follows sets forth numerous embodiments for the inclusion of parenchymal cell cellulose in comestibles. Many others will be apparent to persons of ordinary skill in the art.

Rheology of PCC Compared With Xanthan Gum and Avicel ®

Flow curves (stress as a function of shear rate) were recorded with a Haake RV100 plotter from an M500 viscometer using an MV2 sensor. Shear rates from 14 sec$^{-1}$ to 160 sec$^{-4}$ were modelled with the Casson model to calculate the yield stress value. Subsequently, the power law plastic model was used to calculate the consistency coefficient (viscosity at 1 sec$^{-1}$) and flow behavior index (degree of shear thinning). The range of shear rates is characteristic of those in the mouth during chewing, Burger, Sherman, Morris and Taylor; *Gums and Stabilizers*, (1982).

Figure 2:
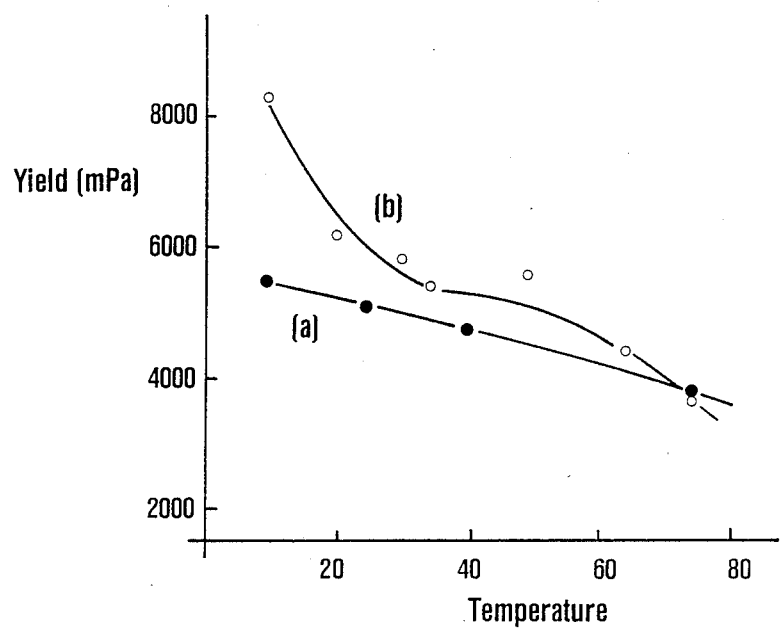
FIG. 2 is a graph showing comparative data for a lower concentration of xanthan gum and PCC.

FIG. 1 shows yield values as a function of temperature for PCC, xanthan gum and Avicel ®. FIG. 2 compares data for a lower concentration of xanthan gum and PCC. Particularly at temperatures associated with storage of foods and consumption of non-hot foods, PCC is dramatic in its higher yield values. This greater structure building property is important both for the shelf stability and for the desired levels of texture required for a wide variety of foods (especially important for "lite" foods where a low level of solids is wanted). Products such as milk shakes, yogurts, puddings, juice concentrates, custards, whipped toppings, icings, jams, etc. are all indicated as candidates for incorporation of PCC to achieve added value. Improved "cling" for salad dressings is indicated in addition to enhanced emulsion stability.

Figure 3:
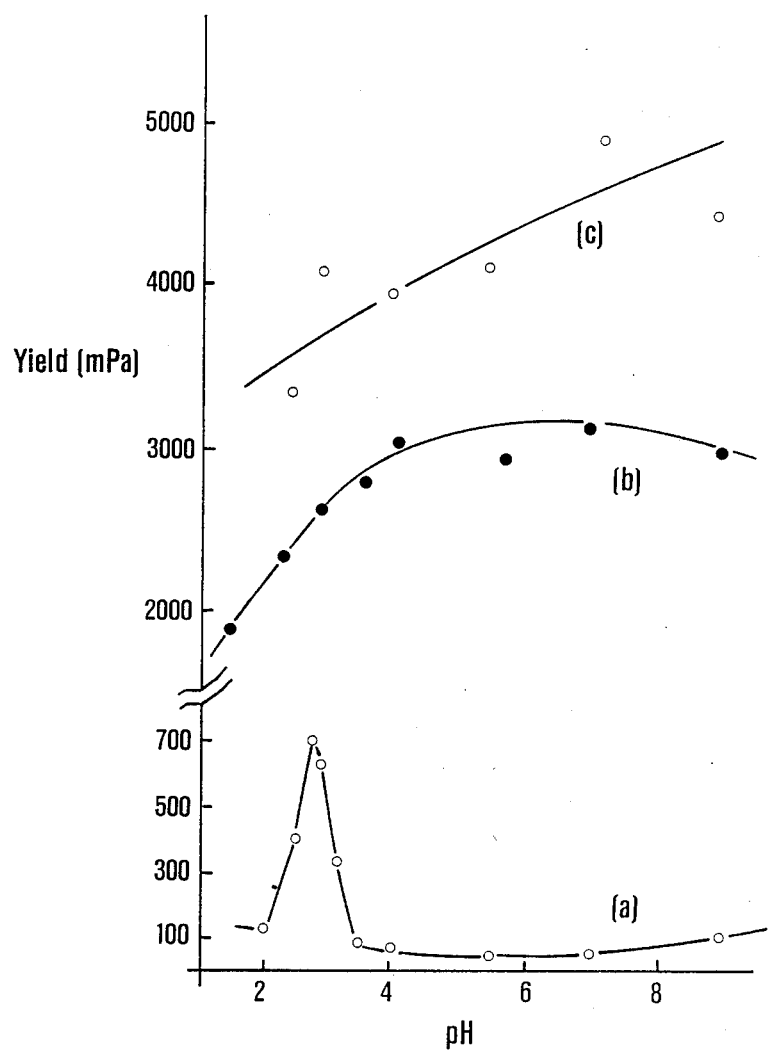
FIG. 3 is a graph showing yield values as a function of pH for PCC, xanthan gum and Avicel ®.

Yield values as a function of pH are shown in FIG. 3. Values for PCC are higher for all pH values examined. Only a slight dependence on pH is noted for PCC and even at the pH values of salad dressing PCC exhibits higher yield, important for stability of cling. A strong dependence on pH Avicel ® for at low pH values likely derives from the CMC that is part of the Avicel ® formulation; a maximum in yield value would be expected on the basis of maximum hydrogen bonding between an equal number of carboxylate anions and protonated carboxyl groups. Such a trend at the law pH values for PCC, which also has CMC added, is not seen since the impact of the CMC is small relative to the very large yield values from the PCC.

Figure 4:
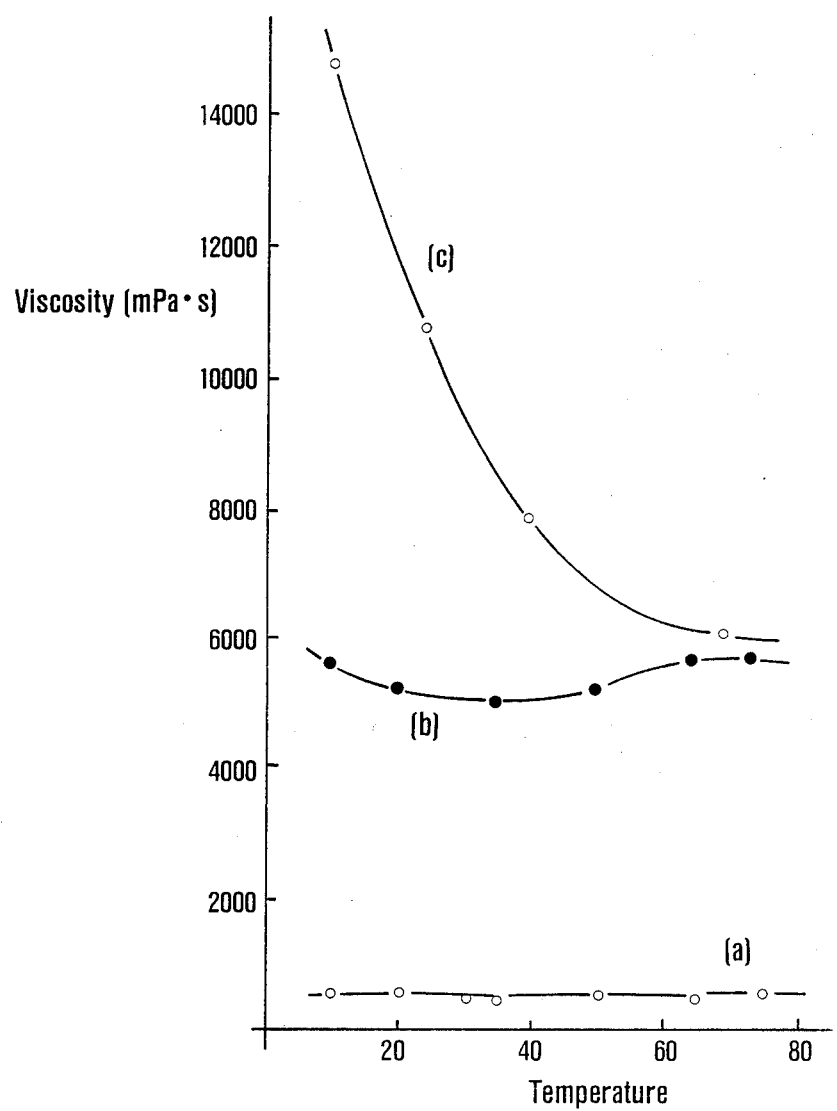
FIG. 4 is a graph depicting flow curves which show viscosity as a function of temperature.

Viscosity at 1 sec$^{-1}$ is shown as a function of temperature in FIG. 4. PCC is consistently more viscous (the same trends are indicated for both 1% and 0.5% concentrations) and has, therefore, better stabilizing ability and textural enhancement via "thickening." A greater thinning with increasing temperature, particularly in the range associated with non-hot foods in the mouth, indicates a more desirable mouthfeel and greater flavor release characteristics. The exceptional viscous properties at low temperatures are again favorable for achieving the texture wanted in those products listed above with respect to yield values.

Figure 5:
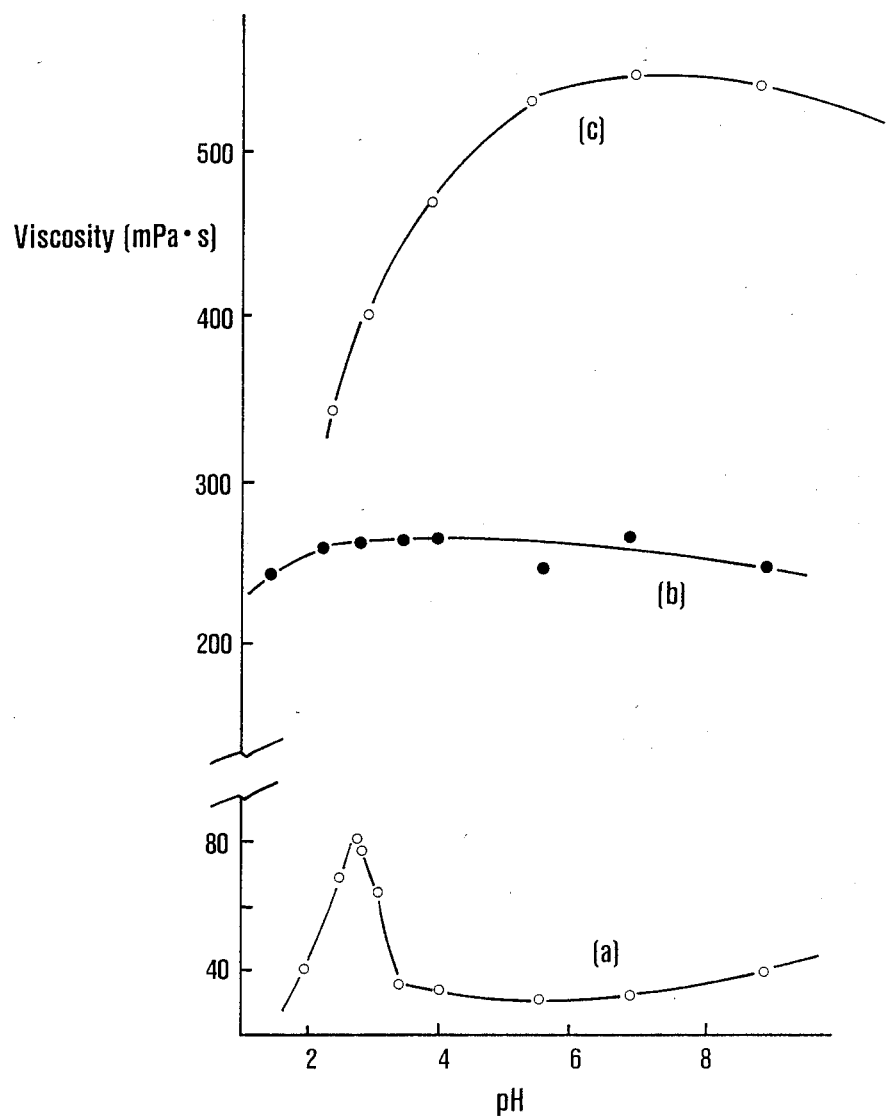
FIG. 5 is a graph showing dependence of viscosity on pH for PCC, xanthan gum and Avicel ®.

Dependence of viscosity on pH, as shown in FIG. 5, indicates PCC as having the greatest texture building properties for all pH values examined. The stronger dependence on pH than is seen for xanthan gum is likely due partly to the CMC. However, the dependence is not steep enough to cause any problems in formulation. Even for pH values found in salad dressings the PCC has greater stabilizing ability than xanthan gum.

FIGS. 6 and 7 show that PCC has shear thinning ability almost identical to xanthan gum and the latter is the most shear thinning of presently allowable food ingredients, Morris and Taylor, *Gums and Stabilizers*, (1982).

Figure 8:
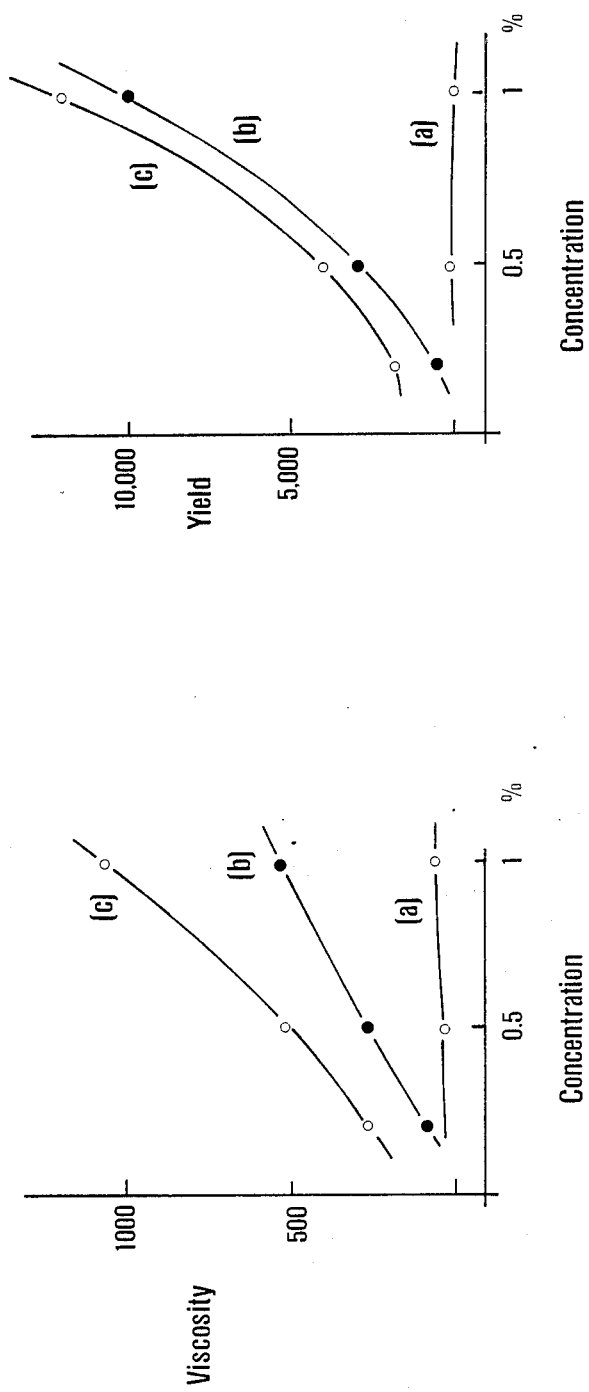
FIG. 8 is directed to two graphs showing concentration dependence of viscosity and yield values.

FIG. 8 indicates concentration dependence of viscosity and yield values. Thus, PCC has consistently superior rheological properties to both Avicel ® and xanthan gum for food texture, stabilization and flavor release. These properties—gel structures (both colloidal and polymer cross-linked), colloidal stabilization, flavor release—make possible both new products that are calorie reduced, have improved mouthfeel, and are easier to process.

Additional data indicate that PCC has an even greater degree of polymeric cross-linking at the molecular level—the high gel modulus values, measured with a Rank shearometer, reflect gelation resulting from interactions at the molecular level, which is analogous to the type of gelation that is achieved with pectin and alginates. The properties indicated by this study are also achieved in emulsions, dispersions, foams, as well as in full product formulations such as puddings, salad dressings, etc. A range of products will benefit by use of PCC. Some of these are:

1. Dairy Products: Viscosity control, smooth texture, and fat mimicry are all enhanced with PCC. Lower levels of PCC would be required than would be necessary with either MCC or xanthan gum. Of special interest would be dairy products with textures such as yogurt, milk shakes, custards and ice creams. The extreme structure building capability of PCC would make possible low calorie formulas: the combination of low required levels and relatively low cost of PCC would have significant cost advantages over the materials presently in use for such purposes. Ice creams are oil-in-water emulsions where the fat is provided by dairy cream: either the dairy proteins or added egg proteins provide emulsification and stabilization. A smooth creamy mouthfeel is partially provided by the emulsified fat droplets. Ice milks which are deficient in the fat phase tend to be less than smooth and less creamy unless other smootheners are added. Smoothness and lightness of texture are enhanced by incorporation of air during freezing of the ice cream and, therefore, "overrun" is normally desirable. In the examples provided, PCC is demonstrated as a partial replacement for dairy cream whereby the PCC may aid in achieving adequate overrun, and/or in providing rich creamy texture.

2. Pourable Dressings: Emulsion stability and flow/cling properties are all enhanced with PCC. Required levels will be less than that required from xanthan gum. Moreover, greater reduction of oil should be easily attained for calorie reduced recipes than is presently possible, while maintaining desirable cling and mouthfeel lubricity.

The data of this study suggest that PCC would make an excellent material on which to base no-oil salad dressing formulations. Levels of 0.2–0.3% PCC (perhaps with approximately 0.1% of another hydrocolloid added to achieve a range of cling and mouthfeel properties) should be adequate for such purposes.

3. Puddings and Desserts: The texture of desserts is attained with a gelling agent. "Cold sets" are derived mostly from gelatin, "heat sets" mostly from starch. To get a range of yield values (the initial "bite," smoothness and "thickness") particulate "fillers" are added—these may be no-fat-dry-milk (NFDM) solids, microcrystalline cellulose (MCC), or emulsified fat droplets. NFDM is an inactive filler in that it does not interact with the gelling matrixif NFDM were used to replace fat, an equivalent amount of NFDM would be used to replace the fat (for classification of fillers as active of "inactive," S. Ring and G. Stainsby, *Prog. Fd. Nutr. Sci.*, 6 (1982), pp. 323–329. MCC, on the other hand, is an active fillerit interacts with other ingredients so that if it were being used to replace fat, much lower levels of the MCC would be required than the amount of replaced fat, while retaining similar texture. It is readily apparent that PCC is an active filler and that even lower levels than required for MCC would be used. Calorie reduction, texture manipulation, and cost reduction would be some of the advantages derived from the use of PCC in dessert products.

4. Whipped Products: Stable aerated products are attained through the use of materials that produce a stabilizing elastic structure surrounding the air globule. Thus, in whipped cream, aggregated fat globules intermingle with protein complexes to provide an elastic structure about the fat globules. In meringues, the structure is provided by protein aggregates—heating at a sufficiently high temperature immobilizes the structure by producing an irreversibly entangles protein matrix. MCC promotes formation of such elastic structures.

PCC has greater potential than MCC for producing stable whipped products. Not only does the PCC give higher yield values required for stable whips, but the greater degree of molecular entanglement shown by the higher gel moduli indicates a higher osmotic pressure will be maintained in the liquid between the air globules (a major mechanism of stabilization in aerated products).

5. Meat Emulsions: These constitute another important class of food products. These emulsions use comminuted meat products and are essentially oil-in-water emulsions. The meat proteins that dissolve in the aqueous phase behave as emulsifiers. Moreover, these proteins aid in the heat effected gelation process that normally is used to bind the product together as a cohesive unit. During the cooking process, loss of liquid can be extensive resulting in "yield loss" with aesthetically undesirable shrinkage. In the examples provided, PCC is demonstrated to help prevent this "yield loss."

6. Confectioneries: PCC has sufficient gel formation potential that partial replacement of pectin may be possible in jams. It would also seem that PCC should find use in certain candies as a means to reduce calorie levels. PCC will also make a good filler for cake icings.

7. Spreads: Spreads are either dispersions of solid particles in a liquid phase, an emulsion where either the fat/oil, or the aqueous phase, may be continuous, or a combination of both. Stabilization of these products is provided by emulsifiers and/or thickeners (e.g., hydrocolloids). High aqueous phase content is a means of providing low calorie products: however, achievement of adequate product stability becomes more difficult at high water contents. In order to function as a spread, spreadability is an important property and the product must, therefore, be malleable and soft, while thick enough in texture to retain shape. In the examples provided, PCC is demonstrated to provide stable, creamy and spreadable dispersions when used in certain formulations.

Overall, PCC has potential for many functional applications in foods. It has properties that will make it superior to either MCC or xanthan gums, two of the "Gold Standards" of the food industry. In general, it is believed that PCC can serve to better effect than either xanthan or MCC in any application where these materials are useful. In addition to the following specific examples, PCC can also be used with positive results as a thickener in jams and other spreads; as a textural enhancer, or as a partial flour replacement in breads and other cakes; as an aid for extrusion of doughs (from its shear thinning ability), and of cereals; as a stabilizer and/or as a textural enhancer for ice creams, salad dressings, etc.; as a suspension aid, stabilizer, and textural enhancer in beverages such as egg nogs, milk shakes, chocolate milk, etc.; as a thickening agent in cooked puddings and instant puddings; as a foam stabilizer in other fat based "whips," protein stabilized foams (e.g., marshmallows, artificial whipped creams, etc.), or other foams used as foods; to provide stability during storage and ease of use for such convenience commodities as prepared cake icings, instant drinks, packaged spreads, etc.; as an aid for frozen meats and fish to avoid deterioration during storage and to improve working performance; as an aid to prevent scorching during cooking of materials such as puddings which contain starch, or other ingredients having a tendency to scorch. Not only does PCC perform where other hydrocolloid materials have become "standards," but it also performs in a more acceptable manner, and in a manner that is unanticipated by an understanding of the existing art.

EXAMPLES

EXAMPLE 1

Isolation of PCC From Spent Sugar Beet Pulp

Spent sugar beet pulp in the form of a dried flake or pellet was employed as a raw material for the isolation of parenchymal cell cellulose (PCC). Fully hydrated sugar beet pulp was adjusted to pH 2.5 with 31% w/w hydrochloric acid at a level of 8-10% w/w dry solids. The feed slurry was pumped at a flowrate of 13.7 pounds per minute through a proprietary plug flow reactor manufactured by St. Lawrence Reactors of Mississauga, Ontario. The reactor consisted of a steam shell and tube, 360 feet of ½ inch OD coil, followed by 40 feet of 1 inch coil and terminated with a 0.160 inch orifice. This provided for a residence time of about 3 minutes with a final temperature excursion up to 160° C. A hydrolysate product containing 11-12% dry solids with a pH of 2.8 to 3 was obtained after flashdown to atmospheric pressure through the discharge orifice.

The hot product was then dewatered using an 18 inch continuous belt press (W. R. Perrin Ltd., Toronto, Ontario). The press cake was slurried with 1 part hot utility water to 1 part cake and again pressed through the belt press. The previous wash steps were repeated resulting in a particulate fraction with only trace amounts of soluble matter remaining.

Bleaching was accomplished using an alkaline solution of 2% w/w sodium hypochlorite ($NaClO_3$). The particulate matter resulting from the second wash step was diluted with hot utility water to form a 2% w/w (dry solids basis) slurry, to which 1 part 2% w/w $NaClO_3$) was added to 1 part slurry, and the mixture allowed to stand over 16 hours.

The bleached slurry was then passed through an 18-inch double stage, vibrating screen separator (Sweco) fitted with a 60 mesh screen on top and a 250 mesh dewatering screen below. Sufficient amounts of utility water were jetted onto the top stage to facilitate classification of the fibrous cellulose (+60 mesh) from the membranous cellulose—(−60 mesh. +250 mesh). The resulting PCC gel obtained from the second stage of the Sweco unit was dewatered to a press cake at 12-20% w/w solids with the continuous press and the moist cake stored at 4° C. until used.

EXAMPLE 2

Isolation of PCC From Spent Citrus Pulp

The established protocol for isolating PCC from limed spent citrus pulp is similar to Example 1. PCC from this feedstock is readily prepared by either alkaline or acidic reactor conditions. However, alkaline saponification conditions allow concomitant hydrogen peroxide bleaching during the initial reaction. To 200 pounds of citrus pulp at 9.4% w/w (non-volatile dry solids) was added 113 pounds of utility water, 1000 ml 50% w/w caustic soda solution, and 14.3 pounds 35% w/w $H_2O_2$ solution.

The resultant 6.08% w/w (dry solids) feed slurry with a pH of 10.3 was then pumped through the steam/tube reactor having a coil configuration consisting of a 240 foot length of 1-inch OD tubing terminated by a single 0.160 inch orifice/impact plate. A Moyno type feed pump operating at 190 rpm resulted in a residence time of 151 seconds and the reactant slurry reached a temperature of 166° C. The flashed product was found to have a 7.35% w/w nonvolatile matter (dry solids basis) at a pH of 5.46.

The hot product was then dewatered using the belt press followed by dilution with hot water and resuspended into a pourable slurry. After pH adjustment to between 10 and 11 with caustic soda, a secondary $H_2O_2$ bleaching step was conducted for 16 hours. The ratio of $H_2O_2$ to PCC solids was 1 to 1. The bleached PCC was then washed and separated from fibrous forms of cellulose using a 30 inch double stage Sweco fitted with a 28 mesh screen on top and a 250 mesh dewatering screen below. The collected PCC fraction was dewatered to an 8.02% w/w (dry solids basis) cake using the belt press and then stored at 4° C. until used.

EXAMPLE 3

PCC Rheology Synergism With Cellulose Ethers & Pectin

Using the bleached PCC of Example 2, a series of homogenates was prepared with three commercially available carboxymethyl celluloses (CMC) obtained from Sigma Chemical Company designated low (lv), medium (mv), and high (hv) viscosity preparations. A 1% w/w solution of each CMC variety was prepared using tap water. Bleached PCC was added to each respective CMC preparation and sufficient tap water added to give final PCC and CMC concentrations of 0.75% w/w/ and 0.1% w/w, respectively. Two reference controls were prepared with only PCC in one and CMC-hv in the other.

Each of the five mixtures was then subjected to 15 minutes of Waring Blender shearing (with the exception of the control, which contained only 0.1% w/w CMC-hv). The homogenates were then cooled to 20° C. and their pH (using a Metrohm model 632 pH-Meter) and rheological measurement (using a FANN model 35A viscometer fitted with an R1 rotor, B1 bob and F1 torsion spring) recorded.

TABLE I

| Sample Description | pH | Visc (cP) @ 1021 1/s | Visc (cP) @ 511 1/s |
|---|---|---|---|
| 0.75% PCC | 8.40 | 37 | 65 |
| 0.1% CMC-hv | 7.86 | 5 | 6 |
| 0.75% PCC, 0.1% CMC-lv | 8.69 | 58.5 | 98 |
| 0.75% PCC, 0.1% CMC-mv | 8.57 | 60.5 | 108 |
| 0.75% PCC, 0.1% CMC-hv | 8.34 | 63.5 | 114 |

Table I above, summarizes the results which lead to the conclusion that a synergistic enhancement of rheological properties occurs with homogenized PCC in the presence of CMC.

Aqueous 1.0% dispersions of Sigma pectin were prepared. Aliquots of this pectin dispersion were added to PCC dispersions to give dispersions containing 0%, 0.02%, 0.05%, and 0.11% pectin, respectively. All dispersions contained 0.2% PCC and were homogenized with a Waring Blender. Viscosities were measured with a Fann viscometer. At a shear rate of 511 sec$^{-1}$ the viscosities of the pectin containing dispersions were essentially identical (14 milliPascal seconds) and about 36% higher than that for the PCC dispersion with no pectin (10.3 milliPascal seconds). Since the viscosities of the pectin containing dispersions were identical, the increase in viscosity, over that of the pectin free dispersion, was not from simple additive viscosities (i.e., the PCC viscosity plus the pectin viscosity), but instead due to an interaction between the PCC and pectin that was complete even at 0.02% pectin.

EXAMPLE 4

Mayonnaise

Mayonnaise contains egg yolk and oil as the two most important functional ingredients. The egg yolk is the emulsifier and the texture is achieved by a high level of oil (the droplets "rub" against each other providing a structure that gives "thickness"). The following formulations were derived from a base recipe (I) by V. D. Kisseoglou and P. Sherman, *J. Texture Studies*, 14 (1983) pp. 397-417. The effects of reduction in both oil level and egg yolk level are demonstrated in test formulations (II, VII): the effects of the addition of PCC (III, IV, V, VI, and VIII) are also demonstrated.

Egg yolk, sugar and salt were introduced into a bowl kitchen mixer and mixed together at high speed for two minutes. One-fifth of the oil was added, dropwise at first and then more quickly. The beater was then operated at slow speed and one-third of the acetic acid-water solution was added. The speed of the beater was increased and another one-third of the acetic acid-water solution was added toward the end of the oil addition. The final one-third of the acetic acid-water solution was added after all the oil had been introduced, whereupon the mixture was stirred slowly for one minute, and then mixed again at high speed for three minutes. Sample X was subsequently homogenized in a Hamilton Beach Blender for 45 seconds on the highest speed and relabeled Xa. Immediately following preparation, the viscosity of each mayonnaise was measured as a function of shear rate (from 9 to 490 sec$^{-1}$. Gel modulus was measured with a Rank Pulse Shearometer, described by S. G. Ring and G. Stainsby, "A Simple Method for Determining the Shear Modulus of Food Dispersion and Gels," *J. Sci. Food Agric.*, 36 (1985), pp. 607-613. The results of these examples demonstrate: (i) the ability to partially replace the oil phase of emulsions with low levels of PCC, thus allowing calorie reduction; (ii) the ability to build texture in food dispersions by low levels of PCC; and (iii) the ability to improve product stability (i.e., less separation of phases) with the addition of low levels of PCC. The textural enhancement by the addition of PC is readily evident. Even at 40% oil (samples V and VI), the addition of 0.40% PCC gave a thicker texture than for the 60% oil control (sample II), and a greater degree of shear thinning. All samples were examined visually after three days and only II, V and VI had some separation of aqueous phase-5 ml for II (40% water), 25 ml for V (60% water) and 10 ml for VI (60% water): thus, increased stability is achieved at higher levels of PCC via higher yield and higher viscosity.

Comparison of X and Xa indicates that increased firmness and gelation is possible also by homogenizing at a higher energy so that smaller droplets of oil are achieved. Optimization of textural and stability parameters are thus readily manipulated by one experienced in the art, principally by increased levels of PCC and to a lesser extent by more efficient means of homogenization, for example, with a Manton Gaulin. For comparison, a commercial mayonnaise was found to have a gel modulus of 1020 N/m$^2$, a yield of 36,000 mPa, an FBI of 0.79, and a CC of 3700 mPa.s.

PCC serves three main functions in these mayonnaise recipes: (i) in replacing part of the oil phase it performs as an "active" filling agent (much lower levels of PCC being required than the amount of oil being replaced) occupying interstitial spaces between the oil droplets; (ii) protection of the oil/aqueous interface is provided by the ability of the PCC to act as an emulsifying agent and interactive component—this is demonstrated by the ability to replace part of the egg yolk which is the principal emulsifying material in mayonnaise: (iii) because of its ability to set up an elastic structure and to increase viscosity, the PCC gives great ability to build texture producing smoothness, creaminess, spreadability, pourability, etc., with these properties all manipulable by one experienced in the art of food emulsions and dispersions.

TABLE A

EXAMPLE 4
Mayonnaise Formulations
(% wt/wt)

| Ingredient | I | II | III | IV | V | VI | VII | VIII | IX | X | XI |
|---|---|---|---|---|---|---|---|---|---|---|---|
| Egg yolk | 6.00 | 6.00 | 6.00 | 6.00 | 6.00 | 6.00 | 4.00 | 4.00 | 6.00 | 4.00 | 6.00 |
| Water | 12.00 | 32.00 | 32.00 | 32.00 | 52.00 | 52.00 | 12.00 | 32.00 | 32.00 | 32.00 | 32.00 |
| Acetic acid | 0.20 | 0.20 | 0.20 | 0.20 | 0.20 | 0.20 | 0.20 | 0.20 | 0.20 | 0.20 | 0.20 |
| Sugar | 1.55 | 1.55 | 1.55 | 1.55 | 1.55 | 1.55 | 1.55 | 1.55 | 1.55 | 1.55 | 1.55 |
| Salt | 0.25 | 0.25 | 0.25 | 0.25 | 0.25 | 0.25 | 0.25 | 0.25 | 0.25 | 0.25 | 0.25 |
| oil | 80.00 | 60.00 | 60.00 | 60.00 | 40.00 | 40.00 | 80.00 | 80.00 | 60.00 | 60.00 | 60.00 |
| PCC | — | — | 0.20 | 0.40 | 0.20 | 0.40 | — | 0.20 | — | 0.20 | 0.20 |
| CMC hv | — | — | — | — | — | — | — | — | 0.10 | — | 0.10 |

TABLE B

EXAMPLE 4

| Recipe | Gel Modulus (SD) (N/m$^2$) | Yield (R$^2$) (mPa) | FBI (R$^2$) | CC (mPa.s) | # data points | pH |
|---|---|---|---|---|---|---|
| I | 1800 (1.4) | 157,000 (0.918) | 0.65 (0.934) | 4950 | 6 | 4.0 |

TABLE B-continued

EXAMPLE 4

| Recipe | Gel Modulus (SD) (N/m$^2$) | Yield (R$^2$) (mPa) | FBI (R$^2$) | CC (mPa.s) | # data points | pH |
|---|---|---|---|---|---|---|
| II | 260 (6.4) | 3,200 (0.964)* | 0.86 (0.938) | 390* | 6 | 4.1 |
| III | 620 (0.7) | 21,000 (0.989) | 0.65 (0.997) | 2075 | 8 | 4.7 |
|  |  | 22,000 (0.984)* | 0.67 (0.994) | 1790* | 6 |  |
| IV | 1200 (0.8) | 52,600 (0.977) | 0.79 (0.961) | 2600 | 8 | 4.6 |
|  |  | 61,000 (0.986)* | 0.64 (0.988) | 3200* | 6 |  |
| V | 440 (2.4) | Viscosity too low to model |  |  |  |  |
| VI | 710 (0.6) | 10,700 (0.999) | 0.61 (0.988) | 865 | 8 | 4.8 |
| VII | 1000 (0.6) | 87,000 (0.987) | 0.63 (0.988) | 7640 | 6 | 4.4 |
|  |  | 81,000 (0.992)** | 0.61 (0.994) | 9200** | 5 |  |
| VIII | 1340 (0.3) | 135,000 (0.995)** | 0.57 (0.995) | 10200** | 5 | 4.4 |
| IX | 470 (4.3) | 20,400 (0.986) | 0.70 (0.993) | 2000 | 8 | 4.9 |
| X | — | 14,300 (0.987) | 0.72 (0.988) | 1370 | 8 | 4.7 |
| Xa | 560 (1.0) | 19,800 (0.988) | 0.69 (0.987) | 1535 | 8 |  |
| XI | 735 (1.1) | 42,900 (0.955) | 0.75 (0.941) | 1640 | 8 | 4.9 |

NOTE:
SD = % standard deviation.
*same number of data used for modelling.
**same number of data used for modelling.

EXAMPLE 5

Emulsions

Some model emulsions demonstrate properties of PCC in comparison to standard hydrocolloids presently on the market. In particular, these "model" emulsions suggest usefulness of PCC in salad dressings, and products of thicker texture such as spreads. The base emulsion used a standard emulsifier, one standard nonionic and one standard anionic.

Model emulsion A: 30% corn oil, 0.3% Polysorbate 60, water.

Model emulsion B: 30% corn oil, 0.3% sodium stearoyl lactylate, water.

Homogenization was achieved with a Manton-Gaulin (Model 15) device operated at 2800-3000 psi for all except A11 and B1-B7, for which 2000 psi was employed. After addition of the emulsion components, the mixture was homogenized for 6 minutes. The first 30% and last 30% of the run were discarded. Flow curves (stress as a function of shear rate), were recorded with a Haake RV100 plotter from an M500 viscometer using an MV2 sensor; all flow curves were at 25° C. Shear rates from 14 sec$^{-1}$ to 160 sec$^{-1}$ were modeled with the Casson model to calculate the yield stress values. Subsequently, the power law plastic model was used to calculate the consistency coefficients (viscosity at 1 sec$^{-1}$) and flow behavior indices (degree of shear thinning). Gel moduli were measured with a Rank pulse shearometer in the variable separation mode. Aliquots of each emulsion were put into test tubes and let stand for forty-eight hours, at which time the amount of separated aqueous phase was measured (normal phase separation). Then, each tube was centrifuged in an IEC clinical centrifuge (model CL) for fifteen minutes at a setting of "7" and the percentage of separation was again measured (accelerated).

These creaming values indicate the ability of PCC to provide stabilization against creaming. At the higher gravitational force in the centrifuge, creaming becomes more evident as the yield of the structure is overcome. It is readily evident that PCC provides a degree of stability observed with very few of the other hydrocolloids employed in this study. The "curdled" appearance of A5 results from incomplete sedimentation of the Avicel® crystals to the bottom of the tube with oil droplets caught among the crystals.

Examination of the rheological parameters demonstrates that PCC has far superior texture building properties to most other hydrocolloids. For the emulsions prepared with Polysorbate 60 and 0.25% of a single hydrocolloid, PCC gives the highest yield, the second highest viscosity, the greatest degree of shear thinning, and second highest gel modulus. CMC hv gave the highest gel modulus reflecting it to be more of a solubilized molecular species and less of a colloidal particle. In the presence of stearoyl lactylate, only xanthan gum gave higher yield and viscosity. An added use for the PCC is seen in combination with certain other hydrocolloids. In the presence of Polysorbate 60 there is a synergism between PCC and the other hydrocolloids, the greatest occurring for CMC. In the presence of the ionic surfactant, the synergism between the PCC and the other hydrocolloids is less than for the corresponding emulsions with Polysorbate 60. Again, however, the greatest enhancement occurs with CMC.

The stabilizing and textural enhancement abilities of PCC occur: (1) by protection of the oil/water interface; (ii) by "actively" filling the spaces between the oil droplets; and (iii) by providing a mechanical (i.e., via enhanced viscosity and/or increased elasticity) barrier to destabilization processes. For those experienced in the art of preparing dispersions or emulsions, it is apparent that PCC provides both great stabilizing ability and great textural enhancement. The former is important for most dispersions and emulsions of technological importance; the latter is especially important for food applications.

TABLE

EXAMPLE 5

| Recipe | Gel Modulus (SD N/m$^2$) | Yield (R$^2$) (mPa) | FBI (R$^2$) | CC (mPa.s) | Percent Separation N | acc | pH |
|---|---|---|---|---|---|---|---|
| A | 0 (—) | 40 (0.985) | 0.77 (0.977) | 30 | 0 | 17 | 7.2 |
| A1 | 50 (16.4) | 130 (0.977) | 0.75 (0.985) | 45 | 49 | 59 | 7.2 |
| A2 | 130 (4.0) | 340 (0.994) | 0.71 (0.996) | 100 | 6 | 30 | 6.1 |

TABLE-continued

| | | | | | | | | |
|---|---|---|---|---|---|---|---|---|
| A3 | 60 | (12.4) | 435 (0.994) | 0.74 (0.997) | 145 | 0 | 16 | 5.4 |
| A4 | 80 | (28.2) | 85 (0.978) | 0.77 (0.983) | 35 | 59 | 64 | 5.4 |
| A5 | 30 | (23.6) | 55 (0.984) | 0.81 (0.988) | 35 | curdled | | 7.0 |
| A5a | 0 | (—) | 20 (0.984) | 0.87 (0.989) | 20 | 0 | 60 | 7.2 |
| A6 | 0 | (—) | 25 (0.983) | 0.87 (0.988) | 25 | 0 | 60 | 7.0 |
| A7 | 0 | (—) | 10 (0.981) | 0.88 (0.985) | 20 | 0 | 1 | 7.1 |
| A8 | 80 | (16.3) | 455 (0.993) | 0.69 (0.996) | 110 | 0 | 23 | 7.0 |
| A8a | 270 | (5.2) | 1,300 (0.998) | 0.66 (0.999) | 265 | 0 | 20 | 7.2 |
| A9 | 0 | (—) | 20 (0.988) | 0.86 (0.987) | 20 | 0 | 19 | 6.9 |
| A10 | 170 | (4.9) | 780 (0.998) | 0.68 (0.999) | 180 | 0 | 20 | 7.0 |
| A11 | 125 | (2.5) | 550 (0.996) | 0.68 (0.998) | 125 | 7 | 35 | 6.4 |
| A12 | 85 | (5.4) | 420 (0.995) | 0.69 (0.996) | 110 | 0 | 10 | 6.6 |
| B | 0 | (—) | 10 (0.990) | 0.87 (0.987) | 20 | 0 | 0 | 6.6 |
| B1 | 90 | (2.9) | 380 (0.993) | 0.66 (0.995) | 75 | 10 | 59 | 6.7 |
| B2 | 135 | (3.3) | 450 (0.997) | 0.72 (0.996) | 140 | 0 | 21 | 6.7 |
| B3 | 65 | (9.2) | 920 (0.991) | 0.67 (0.995) | 180 | 0 | 7 | 6.4 |
| B4 | 55 | (8.1) | 230 (0.980) | 0.70 (0.988) | 60 | 10 | 65 | 6.1 |
| B5 | 60 | (21.9) | 80 (0.989) | 0.76 (0.991) | 35 | 0 | 76 | 6.7 |
| B5a | Not obtained | | 260 (0.992) | 0.69 (0.995) | 70 | 0 | 64 | 6.9 |
| B6 | 0 | (—) | 25 (0.985) | 0.86 (0.988) | 25 | 0 | 6 | 7.1 |
| B7 | 0 | (—) | 125 (0.985) | 0.71 (0.984) | 45 | 0 | 6 | 7.2 |
| B8 | Not obtained | | 615 (0.997) | 0.68 (0.998) | 145 | 0 | 7 | 6.9 |
| B8a | 320 | (10.3) | 2,350 (0.998) | 0.65 (0.999) | 395 | 0 | 19 | 6.9 |
| B9 | 0 | (—) | 60 (0.984) | 0.74 (0.978) | 35 | 0 | 0 | 6.5 |
| B10 | Not obtained | | 1,115 (0.998) | 0.66 (0.999) | 220 | 0 | 25 | 7.0 |
| B11 | 80 | (12.2) | 630 (0.993) | 0.67 (0.996) | 125 | 0 | 42 | 6.7 |
| B12 | 0 | (—) | 175 (0.867) | 0.48 (0.750) | 345 | 0 | 28 | 7.4 |

Additives for Example 5

| | |
|---|---|
| Emulsions A1 and B1: | 0.25% CMC lv |
| Emulsions A2 and B2: | 0.25% CMC hv |
| Emulsions A3 and B3: | 0.25% Xanthan gum |
| Emulsions A4 and B4: | 0.25% Pectin |
| Emulsions A5 and B5: | 0.25% Avicel ® |
| Emulsions A5a and B5a: | 0.50% Avicel ® |
| Emulsions A6 and B6: | 0.25% Methocel F50 |
| Emulsions A7 and B7: | 0.25% Methocel A15 lv |
| Emulsions A8 and B8: | 0.25% PCC |
| Emulsions A8a and B8a: | 0.50% PCC |
| Emulsions A9 and B9: | 0.25% gum arabic |
| Emulsions A10 and B10: | 0.25% PCC/CMC lc* |
| Emulsions A11 and B11: | 0.25% Pectin |
| Emulsions A12 and B12: | 0.25% PCC/Methocel F50* |

*Note:
0.125% each for PC combinations.

EXAMPLE 6

Foam

The ability to aid in foam formation was assessed. One comparison used an egg white base meringue made by mixing at high speed (i.e., whipping in a Sunbeam mix master) 150 ml egg whites for thrice minutes. Then, an aqueous solution containing ¼ teaspoon salt, 50 gm of sugar, and 70 ml of a 0.2% dispersion of the listed hydrocolloids—70 ml water for the control was added. While continuing to whip the egg white, the aqueous mixture was added over about a two minute period. Foam density at room temperature was recorded and an aliquot was baked for seven minutes at 425° C., in a GE Toast-R-Oven, model TR3OB 8411. The nature of the baked meringue was recorded descriptively from visual observation and photographically. A second aliquot was placed in a 600 ml beaker and observed for two hours, at which time the volume of liquid drainage was measured.

| | Density (g/ml) | Drainage (ml) |
|---|---|---|
| Control | 0.19 | 100 |
| Methocel A15 lv | 0.19 | 100 |
| Methocel F-50 | 0.20 | 100 |
| CMC lv | 0.19 | 85 |
| CMC hv | 0.18 | 90 |
| Xanthan gum | 0.18 | 30 |
| Avicel ® | 0.18 | 80 |
| PCC | 0.18 | 80 |

The foam value was maintained in all cases except for the two Methocels. In general, there was not any significant difference noted between PCC and the other hydrocolloids except for the Methocels, which were significantly inferior. After baking, the two meringues with Methocel had badly collapsed and the liquid had drained to the bottom of the pan. It is apparent that in those applications where egg white foams are prepared in the presence of hydrocolloids, that PCC performs at least as well as those hydrocolloids that presently provide acceptable properties.

EXAMPLE 7

Whips

In a second whipping test, a commercial 35% butterfat whipping cream was used. A 63.2 ml. aliquot was diluted with a series of aqueous dispersions of hydrocolloids (136.8 ml) to give a final 200 ml volume of 12% butterfat and 0.25% hydrocolloid. After refrigeration at 4° C. for 20–40 hours, 200 ml of each was whipped at high speed in a cold bowl for four minutes with a Sunbeam Mixmaster at a setting of 9. Foam density was recorded; an aliquot was put in a bottle inverted over a 18 mesh screen, and levels of drained liquid recorded with time.

| Hydrocolloid | Density (mg/ml) | Volume Measured (ml) | Drainage 0 hr–2 hr | | Final Foam Volume (ml) |
|---|---|---|---|---|---|
| None (full cream) | 425 | 325 | 0 | 1 | 325 |
| Water (control) | 68 | 255 | 175 | 153 | 30 |
| CMC hv | 638 | 270 | 5 | 110 | 160 |
| Xanthan gum | 622 | 265 | 0 | 5 | 320 |
| Pectin | 676 | 265 | 50 | 150 | 160 |
| Avicel ® | 574 | 320 | 110 | 155 | 100 |
| Methocel F50 | 684 | 265 | 150 | 155 | 35 |
| Methocel A15 lv | 536 | 325 | 150 | 155 | 35 |
| PCC | 510 | 325 | 0 | 90 | 265 |

In these examples, the reduction of butterfat content to 12% gives the range of normal coffee cream (butterfat content of 10–18%), and whipability normally considered to be essentially absent at this level. This was demonstrated by the control where the density indicates very little air has been incorporated during whipping. PCC gave the maximum benefit over the control sample (12% butterfat, no PCC). Although xanthan gum gave more retained foam at the end of two hours, the foam was extremely runny and had no tendency to hold peaks. The PCC foam that was retained on the screen, on the other hand, was able to hold its shape when formed into peaks. These foams demonstrate: (i) the ability of PCC to act as a fat replacer; (ii) the ability of PCC to aid in achieving high overruns in foams; and (iii) the ability of PCC to build elastic structure required for foam stabilization, i.e., it acts as a foam stabilizer.

EXAMPLE 8

Cakes and Breads

A standard cake recipe as given by O. Hughes, *Introductory Foods*, 4th ed., MacMillan Co., New York, 1962, was used to demonstrate the ability of PCC to improve elastic properties of baked goods. The control recipe consisted of:

| | |
|---|---|
| 1 cup sugar | ¼ tsp. salt |
| ⅓ cup liquid fat | 2 ½ tsp. baking soda |
| ⅔ cup milk (skim) | ½ tsp. flavoring |
| 2 cups cake flour | |
| 2 eggs (medium size) | |

The milk and PCC were blended in a Viking blender ("liquify" setting) for five minutes. The eggs and fat were then added and blended with a Sunbeam Mixmaster for an additional one minute. This liquid mix was poured over the remaining ingredients in a mixing bowl and mixed for 45 seconds at the low setting of "stir" and for an additional 75 seconds at a higher setting of "mix." Each cake was baked at 375° F. for 57 minutes in a greased and floured loaf pan (8"×4")—the oven had been held at 375° F. for one hour prior to baking of cakes. The cakes were removed from their pans after cooling for 14 hours. Prior to removal, the bottoms of the pans were heated for a very short time until the pan felt warm to the hand. Five cakes were made with formula changes as following. Recipe 5-1 had no changes from the above ingredients.

| | Oil | Flour | Eggs | Milk | Water |
|---|---|---|---|---|---|
| 5-1 | Crisco | 2 cups | 2 | ⅔ cup | None |
| 5-2 | Crisco | 1 ½ cups | 2 | ⅔ cup | None |
| 5-3 | Crisco | 1 ½ cups | 2 | ⅔ cups @ 2% PCC w/w | None |
| 5-4 | Corn | 1 ½ cups | 1 | ⅔ cups | 2 tbsp. |
| 5-5 | Corn | 1 ½ cups | 1 | ⅔ cups @ 2% PCC w/w | 2 tbsp. |

The following observations were made. Both 5-2 and 5-4 tended to stick to the pan and the bottoms of these cakes tore on removal from pans. The tops of both these cakes were sticky and "candied" in appearance with "pits" where surface boiling had occurred—neither had a cake-like appearance. Cake 5-2 had a non-uniform dark brown color, while 5-4 was a uniform golden brown color. On cooling there was some volume reduction for both 5-2 and 5-4, with the tops of the cakes falling and leaving raised (curled) corners; separation from the pan sides was about 3–4 mm. Recipes 5-1, 5-3 and 5-5 all had a normal cake-like appearance. They were uniformly golden brown in color, with raised centers and some cracking in the middle, and no reduction in volume on cooling. The separation from the pan sides was about 1–2 mm. Removal of cakes from the pans was easy and without any tearing. Cake 5-2 was the darkest in color; 5-4 was intermediate between 5-2 and the others. Slicing of the cakes also indicated 5-1, 5-3 and 5-5 to be easily sliced, giving a firm, good quality slice. Both 5-3 and 5-5 felt slightly moister than 5-1 which was fairly dry. Cakes 5-2 and 5-4 yielded slices that tended to be spongy in appearance and overly rubbery in texture.

Angel cakes were also prepared using the following base (standard) recipe from *Joy of Cooking*, Rombauer and Becker, The New American Library, Inc., 1973. The ingredients and order of addition were:

1 ¼ cups sifted granulated sugar;
1 cup cake flour sifted twice, and then again with one half of above sugar and ½ tsp salt;
1 ¼ cups of egg whites, plus 2 tbsp. water were whipped (setting 12 on Sunbeam Mixmaster) until stiff, then 1 tsp. cream of tartar was added while continuing to whip.
½ tsp. each of vanilla and almond flavoring were then added.

The Mixmaster was changed to the slow "Fold" setting and the remaining flour-sugar mixture was added 1 tbsp. at a time. After all the ingredients were added and blended, the batter was poured into a tube pan and baked for 50 minutes at 350° F. The pan was removed from the oven and suspended upside-down for 1 ½ hours. The cake was then removed by sliding a knife around the edges to loosen the cake from the pan. The standard cake is called recipe 5-6. A second angel cake (recipe 5-7) was made replacing ½ cup of the egg white with water. The water was added after first whipping the ¾ cup of egg white with the 2 tbsp. water to stiffness. The remainder of the procedure was the same as for recipe 5-6. A third cake (recipe 5-8) was made with recipe 5-7, using ½ cup of 2% PCC w/w (aqueous) in place of the ½ cup of water. Recipe 5-6 gave a uniformly golden cake that did not shrink from the sides of the pan on cooling with a texture that was soft, light and not rubbery. The cake from recipe 5-7 was a darker brown and shrank away from the sides of the pan by about 3-4 mm during cooling. Its texture was hard and rubbery. Recipe 5-8 looked almost the same as 5-6 with about 1 mm of shrinkage only at the very top of the cake. Its texture was much softer than 5-7 (slightly firmer than 5-6), and was not rubbery (very similar to 5-6). The diameter of the tops and the heights of the cakes were as follows:

Standard Recipe 5-6: 203 mm diameter×75 mm height.

Control Recipe 5-7: 186 mm diameter×56 mm height.

PCC Recipe 5-8: 202 mm diameter×64 mm height. PCC gave an obvious improvement over the control recipe and suggests possible use as a partial replacement for egg white. The ability of PCC to form the necessary elastic structure to stabilize the foam is exhibited. While the flour also contributes to this structure, as seen in recipe 5-7, flour produced unacceptable results when egg white is reduced without the addition of PCC. A low level of PCC (0.4% level in the water) was used to replace a much higher level of egg white solids. For example, liquid egg white contains about 12% solids, most of which is composed of the three proteins albumin, conalbumin and ovomucoid.

Three bread recipes were prepared, all containing 2 tablespoons sugar, 1½ tablespoons of butter, 1½ tablespoons shortening, 1 cup scalded milk, and ¼ cup 30° C. water with 1 package of Fleishmann's Rapidmix TM "Active Dry Yeast": (i) a standard recipe containing 6 cups flour and 1 cup water; (ii) a control recipe containing 4 cups flour and 1 cup water; (iii) a test recipe containing 4 cups flour and 1 cup of 1% PCC. Each recipe was prepared by a normal home breadmaking procedure with kneading, proofing, molding, a second proofing, and finally baking. Whereas the control recipe: (ii) was almost not breadlike with dough being too fluid for proper kneading and the final baked loaf of low volume and very poor texture, the test recipe gave a dough that was able to be kneaded and the final loaf volume was close to that of the standard loaf and also possessed a texture similar to the standard loaf.

In another experiment, from 0.2% to 1% levels of PCC were added to a wholemeal bread for examining the results on crumb quality. It was found that the crumb of the PCC bread was much firmer than that of the control which contained no PCC, suggesting possible use of PCC for breadings and coatings where a firm crumb is desirable.

In yet another experiment, 0.04% and 0.08% levels of PCC were respectively added to two wholemeal bread doughs. The control bread contained no PCC. It was found that after four days of storage of the breads, those containing PCC had softer crumb quality than did the control, i.e., those containing PCC gave the perception of having aged less than the control.

EXAMPLE 9

Puddings and Pie Fillings

Puddings were prepared using a simple starch recipe (also from R. M. Griswold). Cornstarch (36 gm) and sugar (150 gm) were mixed together and 711 ml of water was added gradually. The mixture was cooked over direct heat. It was stirred constantly until the mixture had boiled for several minutes and was almost clear. After cooling to 42°±2° C., which required 20 minutes, a portion was poured into the cell of a Rank pulse shearometer and the gel modulus value was measured as described by S. G. Ring and G. Stainsby, "A Simple Method for Determining the Shear Modulus of Food Dispersions and Gels," *J. Sci. Food Agric.*, 36 (1985), pp. 607-613. The measurements were made both immediately and after an additional 20 minutes (values in brackets). To observe the effect of PCC, ¼ of the starch was replaced with PCC at 0.2% and 0.3% in the water. The control was prepared with reduced starch, but no PCC.

| Starch (g) | Sugar (g) | Water (ml) | PCC (g) | Gel Modulus (N/m²) | |
|---|---|---|---|---|---|
| 36 | 150 | 711 | 0 | 150 | (150) |
| 25 | 150 | 711 | 0 | 90 | (70) |
| 25 | 150 | 711 | 1.42 | 100 | (120) |
| 25 | 150 | 711 | 2.13 | 150 | (170) |
| 25 | 150 | 711 | 1.42* | 150 | (150) |

*Also with 0.36 g CMC hv

Samples containing no PCC required constant stirring in order to keep the starch suspended, and to prevent scorching and clumped gel "balls" from forming on the bottom. These give a lumpy pudding. An obvious advantage of incorporating PCC was that the starch remained suspended without stirring, and there was almost no tendency towards forming clumps even if stirring were discontinued for over half of the cooking time. Although the pudding texture is not completely described by the gel modulus, this parameter does give a measure of the relative degree of gelation, particularly at the molecular level (i.e., the interacting "unit" forming the gel would be sub-microscopic in size). It is readily apparent that PCC could be used as a partial replacement for starch in such formulations. Moreover, it would function to make the preparations of such products easier where it helps to keep ingredients suspended. PCC not only helps build texture in these puddings, but it can partially replace starch, with much less PCC being required than the amount of starch removed.

A control apricot pie filling was made using 60% apricot pulp, 10% granulated sugar, 3.4% starch, 0.015% saccharin and 26.505% water. Starch and water were heated, with constant stirring, to effect gelatinization of the starch. The other ingredients were then added. After reheating for a brief period, the product was cooled. A test apricot pie filling was made similarly, but with only 0.7% starch and 0.25% PCC. The product containing the PCC was noted to have improved flavour release, along with an improved texture, giving a cleaner flavour when compared to the control.

EXAMPLE 10

Icings

Cake icings were prepared by creaming 1 tablespoon of margarine with 135 grams of Lantic TM icing sugar and 26 ml of an aqueous phase. Five aliquots each about 20% of icing sugar and aqueous phase were creamed with a rubber spatula between each addition. Recipe 8-1 used water as the aqueous phase. Recipe 8-2 used 1% PCC in water as the aqueous phase. Both preparations were placed in a refrigerator. After four days, visual examination of the icings indicated considerable granularity in 8-1, apparently from separation of fatty globules from the aqueous phase. Icing 8-2 was smooth and creamy. After an additional week, the fat in 8-1 had almost completely separated, whereas 8-2 remained creamy and still spreadable. PCC again functioned as a stabilizer of the fat emulsion in the icing. It also provided a smoother icing with both better spreadability and better shape retaining ability.

EXAMPLE 11

Ice Cream

Ice creams were formulated using standard recipes provided with a Waring Ice Cream Parlor ™. Each recipe contained either 2 cups (formulas 1 to 10 inclusive), or 1 cup (formulas 11 to 15 inclusive) sugar, $1\frac{1}{2}$ tsp. vanilla extract, and $\frac{1}{8}$ tsp. salt. Modifications were made to demonstrate the effects of PCC addition. For each recipe, the ingredients were placed into the metal bucket and stirred to dissolve the sugar. Then ice was layered around the metal bucket alternately with Sifto ™ pickling salt (total of 500 g salt except for recipe 7a where 300 g was used) and 2 cups of water so that the ice/salt mixture came to the top of the metal bucket. The ice and salt were layered, while the metal bucket was rotated. The time required for the ice cream to freeze (at which time the equipment automatically shut off) and the weight of 1210 ml of the ice cream was recorded. Recipes 2 and 4 were repeated at double the normal volume. The combined mixture was homogenized at 1600 psi for 5 minutes on a Manton Gaulin (MG) homogenizer. An aliquot of the homogenized mixture was then put into the ice cream maker and frozen as in the regular recipes.

The table below summarizes the ingredients variation made in order to study the results of PCC addition to ice creams. The following table provides a summary of important observations. It is readily apparent that PCC gives positive results over the respective controls in all cases. These positive results include increase in overrun, and/or increase in creaminess, and/or increase in smoothness.

|            | 1*  | 2[1] | 3   | 4   | 5[2] | 6   | 7   | 8*  |
|------------|-----|------|-----|-----|------|-----|-----|-----|
| Homo milk  | —   | —    | —   | —   | —    | —   | —   | 4c  |
| 10% cream  | 2c  | —    | —   | —   | 2c   | 2c  | 2c  | —   |
| 18% cream  | —   | —    | —   | —   | —    | —   | —   | —   |
| 35% cream  | 2c  | 2c   | 2c  | 2c  | —    | —   | —   | —   |
| Eggs       | —   | —    | —   | —   | —    | —   | —   | —   |
| Water      | —   | 2c   | —   | —   | 2c   | —   | —   | —   |
| 0.5% PCC   | —   | —    | 2c  | —   | —    | 2c  | —   | —   |
| 0.25% PCC  | —   | —    | —   | 2c  | —    | —   | 2c  | —   |
| Pudding    | —   | —    | —   | —   | —    | —   | —   | —   |

|            | 9[3] | 10  | 11* | 12  | 13* | 14[4] | 15  | 7A  |
|------------|------|-----|-----|-----|-----|-------|-----|-----|
| Homo milk  | 2c   | 2c  | 2c  | 1c  | —   | —     | —   | —   |
| 10% cream  | —    | —   | —   | —   | 2c  | —     | —   | 2c  |
| 18% cream  | —    | —   | —   | —   | 2c  | 2c    | 2c  | —   |
| 35% cream  | —    | —   | —   | —   | —   | —     | —   | —   |
| Eggs       | —    | —   | 2   | 2   | 2   | 2     | 2   | —   |
| Water      | 2c   | —   | —   | —   | —   | 2c    | —   | —   |
| 0.5% PCC   | —    | —   | —   | —   | —   | —     | —   | —   |
| 0.25% PCC  | —    | 2c  | —   | 1c  | —   | —     | 2c  | 2c  |
| Pudding    | —    | —   | $\frac{1}{2}$ | $\frac{1}{2}$ | —   | —     | —   | —   |

*Standard recipes
(#1 for 2, 3, 4, 5, 6, 7 & 7a);
(#8 for 9, 10);
(#11 for 12);
(#13 for 14 & 15).
[1]Control recipe for #3, 4.
[2]Control recipe for #6, 7.
[3]Control recipe for #10.
[4]Control recipe for #15.

For ordinary vanilla ice cream the PCC formulations gave superior overrun. To provide richer textures, it appeared that lower PCC levels would be better if higher overrun were desired, for example, recipes 4 and 7 gave higher overrun than recipes 3 and 6, respectively. In any case, PCC increases smoothness and richness of texture.

| Recipe | Time to Freeze (Min.) | Weight/ 1210 ml (grams) | Texture | Comment |
|--------|-----------------------|-------------------------|---------|---------|
| "Ordinary Vanilla" | | | | |
| 1 | 50 | 891.6 | v. smooth, v. thick, v. creamy | Standard |
| 2 | 40 | 1012.8 | coarse, shiny (icy), creamy | Control |
| MG* | 30 | 1118.9 | creamy, firm | Control |
| 3 | 40 | 975.3 | smooth, v. thick, v. creamy | Test |
| 4 | 37 | 975.3 | smooth, v. thick, v. creamy | Test |
| MG* | 35 | 1058.5 | v. creamy, firm | Test |
| 5 | 45 | 1047.3 | coarse, heavy, shiny (icy) | Control |
| 6 | 50 | 1052.0 | smooth, v. thick, creamy | Test |
| 7 | 40 | 1114.0 | smooth, thick, creamy | Test |
| "Vanilla Ice Milk" | | | | |
| 8 | 35 | 1151.2 | shiny (icy), almost creamy | Standard |
| 9 | 35 | 1173.0 | v. icy, coarse | Control |
| 10 | 30 | 1206.7 | icy, creamy | Test |
| "French Vanilla With Pudding" | | | | |
| 11 | 35 | 1168.0 | smooth, v. thick v. creamy | Standard |
| 12 | 22 | 1163.2 | smooth, v. thick, v. creamy | Test |
| "French Vanilla Without Pudding" | | | | |
| 13 | 30 | 982.7 | smooth, v. thick, creamy | Standard |
| 14 | 27 | 1057.6 | coarse, thick, rough, | Control |
| 15 | 20 | 1062.5 | smooth, v. thick, creamy | Test |
| 7a | 47 | 1068.7 | smooth, v. thick, creamy | Test |

*MG - ice cream was homogenized on Manton Gaulin prior to freezing.

After one month of storage in a chest freezer, comparisons were made of the controls with the respective test formulations. In the case of recipes 1, 2, 3 and 4, all tended to be similar in texture and very creamy. On melting, 4 and 3 gave a slightly creamier "melt" than did 2, which gave a curdled appearance.

In the case of recipes 5, 6 and 7, 7 was the firmest without being hard; 5 was hard and very icy in texture. Both 6 and 7 were creamier and had a silkier appearance as they melted (6 was creamiest of all). Recipe 5 was coarse in appearance. The "melts" from 6 and 7 were both creamy, that from 5 was watery and curdled.

In the case of recipes 11 and 12, 12 was firmer and heavier in texture. On melting, 11 gave a more curdled (separated) appearance, and 12 was creamier.

In the case of recipes 13, 14 and 15, 14 and 15 were similar, both firmer than 13. As melting proceeded, 15 was creamier in appearance than 14.

Use of the Manton Gaulin for homogenization prior to freezing gave firmer ice creams than when the corresponding recipes were simply stirred prior to freezing.

EXAMPLE 12

Spreads

An assessment of PCC use in spreads was made by making 50/50 dispersions of corn oil and water with 2% PCC and 0.5% of surfactant. For each surfactant, 1 g was dissolved (or dispersed) in 100 g corn oil. To this were added 50 g of 8% PCC (aqueous), and 50 ml water using the lowest setting ("1") on the Hamilton Beach blender. The entire mixture was then blended for minutes at the highest setting ("7"). Observations were made at 1 hour and again after three days of storage in the refrigerator. A summary of results follows.

Adogen® 432 (quaternary ammonium compound from Sherex Chemical Co. Inc.)—Curdled, oil separation after 3 days, none immediate.

Alkamuls STO (sorbitan tri-oleate ester from Alkaril Chemicals Ltd.), HLB 1.8—Curdled, oil separation: similar at 1 hr. and at 3 days.

Alkamuls GMO-45 (glycerol mono-oleate from Alkaril Chemicals Ltd.), HLB 3—Curdled, oil separation: similar at 1 hr. and at 3 days.

Alkamuls SMO (sorbitan monooleate from Alkaril Chemicals Ltd.), HLB 4.3—Somewhat curdled, slight separation.

Alkaquat DMB 451 (alkyl benzyl dimethyl ammonium quaternary chloride from Alkaril Chemicals Ltd.)—Somewhat curdled, slight oil separation.

Alkaphos L3-64A (Aliphatic phosphate ester from Alkaril Chemicals Ltd.)—Slightly curdled, tending towards creaminess, a little oil separation; but stable, very creamy and thick with 2% surfactant.

Canamulse 55 (propylene glycol mono fatty acid esters from Canada Packers Inc.), HLB 3.5—Curdled, a lot of oil separation.

Canamulse 100 (mono & diglycerides from Canada Packers Inc.), HLB 2.8—Curdled, oil separation: similar at 1 hr. and at 3 days.

Canamulse 110 (mono & diglycerides from Canada Packers Inc.), HLB 2.8—Curdled, a little oil separation: more oil separation at 3 days.

Canamulse 155 (mono & diglycerides from Canada Packers Inc.), HLB 3.8—Curdled, a lot of oil separation.

Clearate B-60 (lecithin from W. A. Cleary Corp.)—Curdled, oil separation: similar at 1 hr. and at 3 days.

Crodesta F-50 (sucrose distearate from Croda Canada Ltd.), HLB 7—Curdled, oil separation: similar at 1 hr. and at 3 days.

Crodesta F110 (sucrose monostearate from Croda Canada Ltd.), HLB 11—Curdled, oil separation: similar at 1 hr. and at 3 days.

Crodesta F160 (sucrose monostearate from Croda Canada Ltd.), HLB 14.5—Curdled, oil separation: similar at 1 hr. and at 3 days.

Crodesta SL-40 (sucrose monococoate from Croda Canada Ltd.), HLB 15—Stable, thick and creamy, holds peaks, v. little oil separation, no increase with time.

Emerest 2381 (propylene glycol monostearate from Emery Industries, Inc.), HLB 4.0—Very curdled, separated and unstable.

Emsorb 2500 (sorbitan monooleate from Emery Industries, Inc.), HLB 4.6—Curdled, thick, oil separation.

Emsorb 2502 (sorbitan sesquioleate from Emery Industries, Inc.), HLF 4.5—Curdled, thick, oil separation.

Emsorb 6901 (POE(5) sorbitan monooleate from Emery Industries, Inc.), HLB 10—Stable, thick, creamy.

Hodag GMO-D (glycerol monooleate from Hodag Chemical Corp.), HLB 2.7—Curdled, oil separation: similar at 1 hr. and at 3 days.

Pationic CSL (calcium stearoyl lactylate from C. J. Patterson Co), HLB 5.1—Not very curdled: little oil separation.

Pluradyne NP-40 (nonylphenol ethoxylate from BASF Chemicals), HLB 18—Stable, thick and creamy at 1 hr.: some oil separation after 3 days.

Pluradyne NP 100 (nonylphenol ethoxylate from BASF Chemicals), HLB 19—Stable, thick and creamy at 1 hr: oil separation after 3 days.

Pluronic® 10R5 (block copolymer propylene/ethylene oxides) from BASF Canada Inc.), HLB 2-7, Curdled, oil separation: similar at 1 hr. and at 3 days.

Pluronic® 17R1 (block copolymer propylene/ethylene oxides) from BASF Canada Inc.), HLB 2-7—Curdled, oil separation: similar at 1 hr. and at 3 days.

Pluronic® 25R1 (block copolymer propylene/ethylene oxides) from BASF Canada Inc.), HLB 2-7—Curdled, oil separation: similar at 1 hr. and at 3 days.

Pluronic® 31R1 (block copolymer propylene/ethylene oxides) from BASF Canada Inc.), HLB 2-7—Curdled, oil separation: similar at 1 hr. and at 3 days.

Pluronic® L35 (block copolymer propylene/ethylene oxides) from BASF Canada Inc.), HLB 19—Stable, thick and creamy.

Pluronic®L122 (block copolymer propylene/ethylene oxides) from BASF Canada Inc.), HLB 4—Stable, thick and creamy.

Sandopan B (anionic, sodium salt from Sandoz)—Very unstable, very curdled, no dispersion of PCC.

Span 40 (sorbitan monopalmitate from Atkemix Inc.), HLB 6.7—Curdled, oil separation: similar at 1 hr. and at 3 days.

Span 60 (sorbitan monostearate from Atkemix Inc.), HLB 4.7—Curdled, oil separation: similar at 1 hr. and at 3 days.

Span 65 (sorbitan tristearate from Atkemix Inc.), HLB 2.1—Curdled, oil separation: similar at 1 hr. and at 3 days.

Span 80 (sorbitan monooleate from Atkemix Inc.), HLB 4.3—Not very curdled. Little oil separation.

Tetronic® 701 (block copolymer propylene/ethylene/ethylenediamine) from BASF Canada Inc.), HLB 3—Curdled, oil separation: similar at 1 hr. and at 3 days.

Tetronic® 901 (a block copolymer propylene/ethylene/ethylenediamine) from BASF Canada Inc.), HLB 3—Not very curdled. Little oil separation.

Tween 20 (POE (20) sorbitan monolaurate from Atkemix Inc.), HLB 16.7—Stable, very thick and creamy.

Tween 21, (POE (4) sorbitan monolaurate from Atkemix, Inc.), HLB 13.3—Curdled, oil separation: similar at 1 hr. and at 3 days.

Tween 60 (POE (20) sorbitan monostearate from Atkemix Inc.), HLB 9.6—Curdled, oil separation: similar at 1 hr. and at 3 days.

Tween 61 (POE (4) sorbitan monostearate from Atkemix Inc.), HLB - 9.6—Curdled, oil separation: similar at 1 hr. and at 3 days.

Tween 85 (POE (20) sorbitan trioleate from Atkemix Inc.), HLB 11.0—Not very curdled. Little oil separation.

Thus, certain emulsifiers, especially those with an HLB value above about 15, allow sufficient stabilization: Alkaphos L#-64A, Crodesta LS-40, Emsorb 6901, Pluradynes NP-40 and NP 100, Pluronics L35 and L122, Tween 20 and Tween 60. Emulsions formed with these, but without any PCC, are very runny and liquid. However, emulsions formed with PCC had the consistency of a fairly thick mayonnaise. Such formulations provide a base to which may be added other ingredients to provide a range of spreads and dips. For example, addition of Kraft dinner cheese powder provides a type of cheese spread. Variation in the level of ingredients, including the level of PC, provides a wide range of consistencies.

Further recipes were formulated using two emulsifiers. Emulsifier I was added to 100 g of 8% (aqueous) PCC. This was added to 100 ml of water, or 100 ml of an aqueous solution. This aqueous mixture was then added to emulsifier II dissolved in 100 ml of corn oil, while blending at setting "1" on a Hamilton Beach blender. After complete mixing, homogenization was effected at setting "7" for 3 minutes.

| Emulsifier I | | Emulsifier II | | Comments |
|---|---|---|---|---|
| Tween 20 | (2 g) | Span 80 | (1 g) | Thick and creamy, holds peaks, no oil separation. |
| Alkaphos L3-64A | (2 g) | None | | Thick, curdled, a little oiling out. |
| Tween 60 0.5% Klucel G for aqueous phase | (2 g) | Alkaphos L3-64A | (1 g) | Thick, less oiling out than previous examples. |
| Tween 60 0.5% Methocel A15 aqueous phase | (2 g) | Alkaphos L3-64A | (1 g) | Intermediate between two for previous samples. |
| Span 80 | (2 g) | Pluronic 10R5 | (1 g) | Thick, some oiling out. |
| Clearate B-60 | (2 g) | Pluronic 10R5 | (1 g) | Thick, some oiling out. |

Of these emulsions, the best was that prepared with Tween 20 and Span 80, which did not show oil separation even after 1 ½ months.

EXAMPLE 13

Processed Meats

During cooking, meat emulsions (e.g., sausages, frankfurters, etc.), lose fat and water resulting in less juicy products and yield loss. To demonstrate the ability of PCC to help prevent these changes, beef patties were prepared using regular beef hamburger purchased from a meat market. A triplicate moisture analysis indicated a water content of 57.4±0.7%. Four recipes were prepared by mixing the meat by hand with the other ingredients. Patties were formed by pressing the meat into a 3 5/16 inch diameter mold included with a Moulinex "Jeanette." Each patty was individually weighed and then cooked in the center of a Toaster skillet for 5 minutes at a setting midway between 350° F. and 400° F. The cooked patty was then weighed and weight loss was calculated. The following table gives the recipes and the weight losses after cooking. The two test formulations contained a PCC content of 2% and 0.7%.

| | Hamburger (g) | Water (g) | Aq. PCC (7.43%) | Total Water | Salt | No. of Patties (Avg. wt.) | Wt. Loss % |
|---|---|---|---|---|---|---|---|
| 1. | 402.4 | — | — | 57.4% | 1 tsp. | 5 (80.6 g) | 29 |
| 2. | 402.0 | 150.0 | — | 69.0% | 1 tsp. | 6 (91.5 g) | 38 |
| 3. | 405.1 | — | 150.4 g | 67.1% | 1 tsp. | 6 (92.8 g) | 21 |
| 4. | 402.2 | 100.0 | 50.7 g | 68.4% | 1 tsp. | 6 (91.5 g) | 28 |

1. Standard
2. Control
3. Test
4. Test

The appearance of the cooked patties was similar for standard and test recipes. However, for the control samples, there was congealed brown solid material in the liquid which exuded from ("cooked out" of) the patty. This congealed material was gelled protein from the lean part of the beef. The control patties were also noticeably shrunken after cooking relative to any of the other patties after cooking.

It is readily apparent that PCC greatly aids in preventing weight loss during the cooking of these meat patties. In addition, higher levels of water are possible without the undesirable effect of losing valuable protein in the exuded liquid during cooking.

Other meat emulsions were also prepared. A bulk quantity of emulsion was prepared by grinding 4.59 Kg of lean beef with 1.56 kg of port backfat on an Urshel Comitrol ™ 1700 Fitted with a 3 inch cutting head of 0.030-" blade thickness and 0.060-" gap (id. No. 66774 3k030060U). Prior to grinding, the beef and pork fat were cut into 1 inch cubes; any fat or gristle was trimmed from the beef. The material was processed through the Comitrol ™ three times, with handmixing in between, to ensure reasonable homogeneity. Aliquots of this bulk material (homogenate) were then used to prepare the meat emulsions. Additional ingredients were added using dough hooks on a Sunbeam Mixmaster at a speed of "2" (stir) for 3 minutes. PCC material (both 1% and 2% aqueous suspensions prepared from 7.43% PCC) was homogenized on a Waring blender for 15 minutes and cooled to 4° C. prior to preparation of the meat emulsions.

For assessment of these meat emulsions, a modification of the procedure by Raymond et al, *Can. Inst. Food Sc. Technol. J.*, 9 (1976) pp. 216-221 and 13 (1980) pp. 174-177, was followed. Meat emulsions were cooked in 2 5/16 inch diameter Corning ™ 25350 centrifuge tubes from which had been cut the top part just below the tapered section. A wire mesh was fitted at the bottom of the straight side portion so that liquid could drain down into the bottom tapered part of the tube. Meat emulsion was hand stuffed into each tube to an approximate total volume of 125 ml. Then a glass rod was pushed down to the wire mesh in the center of the meat emulsion and a hollow glass tube was inserted into the resulting hole. This allowed pressure release from the bottom cavity to ensure that drainage could occur thereto without resistance. Cooking was achieved by placing the tubes, held in a wire mesh frame so that the top ¼" of the tube was above the water level, into a water bath maintained at 75° C. Cooking time was 40 minutes. After cooking, a spatula was used (if necessary) to make a channel down the side of the cooked emulsion and the liquid was drained into a graduated cylinder. Weights of the uncooked and cooked, drained materials, were compared to calculate weight loss during cooking. The following recipes were used.

| Recipe | Homogenate | Salt | Water | 1% PCC | 2% PCC | Comment |
|---|---|---|---|---|---|---|
| I | 1000 g | 34 g | 182 g | — | — | Control |
| II | 1000 g | 34 g | — | 182 g | — | Test |
| III | 1000 g | 34 g | — | — | 182 g | Test |

Of the drained liquid, the aqueous volume was about 10% greater than the volume of the fat. Results are given in the following table. The addition of PCC gives dramatic increase in yield—i.e., prevents loss during cooking. In addition, it was observed that for recipe I, the cooked meat emulsions were considerable shrunken by about 2 mm from the sides of the tubes. For the test emulsions, no shrinkage from the sides was observed for recipe III and very slight shrinkage for recipe II (about 0.5 mm only at about 20% of the circumference). The cooked product from recipe I was mushier in texture and tended to fracture more on slicing than either II or III: both II and II were almost identical in texture.

| Recipe | Number of Samples | Average Weight Loss | Recovered Liquid Fat | Aqueous |
|---|---|---|---|---|
| I | 5 | 21.6% | 10.1 ml | 13.1 ml |
| II | 4 (0.15% PCC) | 12.8% | 6.8 ml | 7.2 ml |
| III | 5 (0.30% PCC) | 11.5% | 5.9 ml | 6.3 ml |

Use of PCC in meat emulsion such as wieners, sausages, etc. would improve yield on cooking, improve sliceability of such products, and give a "plumper," firmer product of improved texture.

EXAMPLE 14

Coatings/Breadings

Chicken legs were respectively dipped into: (1) water; (ii) 0.2% PCC (aqueous); (iii) 0.5% PCC; and (iv) 1% PCC. After thus wetting, each was coated with Shake & Bake as per instructions accompanying that product. Two chicken legs were used for each (a total of 8 legs). These were baked at 400° F. for 35 minutes and then allowed to cool to room temperature. Considerable juice had exuded from (i); less from (ii); and none from either (iii) or (iv). The juice gelatinized when cool, indicating that proteinaceous materials had been extracted from the chicken meat. The appearance of the coatings was dry for (iv); moist for (i); and intermediate for (ii) and (iii). On cutting through the coatings into the meat, the meat of (i) was drier than the others; that of (iii) and (iv) being the moistest. Consequently, on biting into the chicken legs: (ii) and (iii) were perceived as more plump than either (i) or (iv). The reason (iv) did not appear to be the most plump seemed to be a result of the coating being crumbly and dry on the exterior, with a slightly rubbery "skin" underneath.

Frozen medium sized shrimp were thawed and dipped into either: (i) tap water; (ii) 0.2% PCC (aqueous); (iii) 0.5% PCC; or (iv) 1% PCC. Each was then rolled in bread crumbs and cooked for 3 minutes in a deep fryer containing corn oil maintained at 355° F. After cooking, the shrimp were placed on paper towels to absorb any excess fat. Those from both (i) and (iv) were not crisp and the coating tended to be soggy. The coatings of those from (ii) and (iii) were crispier and gave a "juicer" bite.

EXAMPLE 15

Juices

Dispersions were prepared by adding 1 part (wt) orange juice concentrate (OJC) to 3 parts of aqueous mixtures containing: (a) only water; (b) 0.13% PCC, 0.13% Methocel E15-lv; (f) 0.13% PCC, 0.013% CMC-mv; and (g) 0.13% PCC, 0.013% Klucel. For samples (b) to (g), dispersion was first obtained at Medium speed on a Hamilton Beach Scovil mixer for 10 minutes. After the addition of OJC, mixing was by stirring with a spoon. Aliquots were collected in graduated cylinders. Within 30 minutes, pulp was noted collecting on the bottom of "(a)". Separation was not observed in the others for about 3 hours. After 5 hours, the decreasing order of stabilities was: "(f)"; "(g)"; "(d)"; "(b)"; "(e)"; "(c)"; then "(a)".

Further dispersions of PCC were prepared by diluting 0.74% PCC (no other hydrocolloid, e.g., CMC, present), with water to the concentrations given below. Each dispersion was then homogenized with a Waring Blender for 15 minutes and subsequently de-aerated under vacuum (using an aspirator) for about 5 minutes. To 300 ml of each of these, as well as to 300 ml of similarly deaerated tap water, were added 100 ml aliquots of OJC. A 250 ml aliquot of each of the resulting OJ dispersions was then put into a separate 250 graduated cylinder and allowed to stand.

| Sample | Conc. PCC Dispersion | Conc. PCC in OJ | Clarified Top Volume After 5 hours | 3 days |
|---|---|---|---|---|
| 1. | 0.267% | 0.2% | 0 ml | 0 ml |
| 2. | 0.1333% | 0.1% | 0 ml | 4 ml |
| 3. | 0.0667% | 0.05% | 0 ml | 10 ml |
| 4. | 0.0266% | 0.02% | 0 ml | 65 ml |
| 5. | 0.0% | 0.0% | 80 ml | 174 ml |

It was also observed that all large pieces of pulp (about 2 mm to about 5 mm in size) were on the bottom of sample 5, only a few pieces on the bottom of sample 4, and no pulp was on the bottom of the others after 3 days.

What is claimed is:

1. A stabilized food or drug comestible having at least one of the following properties:
   (a) reduced caloric content;
   (b) reduced fat content;
   (c) improved texture;
   (d) improved flavor release; or
   (e) improved mouthfeel;
said comestible comprised of at least one first material in at least one second material and parenchymal cell cellulose in an amount sufficient to stabilize said dispersion.

2. The stabilized comestible of claim 1, which is a food product.

3. The stabilized comestible of claim 2, wherein said food product is at least one member selected from the group consisting of emulsions, foams, batters and doughs.

4. The stabilized comestible of claim 3, wherein said food product is an emulsion.

5. The stabilized comestible of claim 4, wherein said emulsion is a liquid-in-liquid emulsion.

6. The stabilized comestible of claim 4, wherein said emulsion is a oil-in-water emulsion.

7. The stabilized comestible of claim 4, wherein said emulsion is a water-in-oil emulsion.

8. The stabilized comestible of claim 3, wherein said food product is a foam.

9. The stabilized comestible of claim 8, wherein said foam is comprised of a gas and at least one liquid.

10. The stabilized comestible of claim 9, wherein said foam is a whipped cream product.

11. The stabilized comestible of claim 9, wherein said foam is a whipped cream product and is prepared from at least one dairy product.

12. The stabilized comestible of claim 9, wherein said foam is a whipped cream product and is prepared from at least one nondairy product.

13. The stabilized comestible of claim 3, wherein said food product is a batter.

14. The stabilized comestible of claim 3, wherein said food product is a dough.

15. The stabilized comestible of claim 1, which is a pharmaceutical product.

16. The stabilized comestible of claim 15, wherein the pharmaceutical product is a liquid.

17. The stabilized comestible of claim 15, wherein the pharmaceutical product is a solid.

18. The stabilized comestible of claim 15, which is a drug.

19. The stabilized comestible of claim 1, which contains at least one cellulose ether.

20. The stabilized comestible of claim 1, which contains pectin.

21. The stabilized comestible of claim 19, wherein said cellulose ether is carboxymethylcellulose.

22. A stabilized food or drug comestible having a reduced caloric or fat content, said comestible comprised of a dispersion of at least one first material in at least one second material and parenchymal cell cellulose in an amount sufficient to stabilize said dispersion.

23. A method for preparing a stabilized food or drug comestible having at least one of the following properties:
    (a) reduced caloric content;
    (b) reduced fat content;
    (c) improved texture;
    (d) improved flavor release; or
    (e) improved mouthfeel;
said comestible comprised of a dispersion of at least one first material in at least one second material, which comprises formulating said comestible to include parenchymal cell cellulose in an amount sufficient to stabilize said dispersion.

24. The method of claim 23, wherein the parenchymal cell cellulose is employed in an amount between about 0.02 and about 20% by weight.

25. The method of claim 23, wherein the parenchymal cell cellulose is employed in an amount between about 0.02 and about 10% by weight.

26. The method of claim 23 for preparing a food or drug comestible having a reduced caloric content while maintaining commercially acceptable physical and processing characteristics comprising formulating said comestible to include at least about 0.02% by weight of parenchymal cell cellulose.

27. The method of claim 23 for preparing a food or drug comestible having a reduced caloric or fat content while maintaining commercially acceptable physical and processing characteristics comprising formulating said comestible to include at least about 0.02% by weight of parenchymal cell cellulose.

28. The method of claim 27, wherein a reduced caloric content is achieved by minimizing the amount of gel forming components needed to prepare said comestible and which comprises substituting for at least a portion of said gel forming components, at least about 0.02% by weight of parenchymal cell cellulose.

29. The method of claim 23 for improving the textural properties of a food or drug comestible comprising adding to the comestible at least about 0.02% by weight of parenchymal cell cellulose.

30. The method of claim 23 for improving the flavor release of a food or drug comestible which comprises adding to said comestible at least about 0.02% by weight of parenchymal cell cellulose.

* * * * *

UNITED STATES PATENT AND TRADEMARK OFFICE
CERTIFICATE OF CORRECTION

PATENT NO.    : 4,923,981                                          Page 1 of 1
DATED         : May 8, 1990
INVENTOR(S)   : Michael K. Weibel and Chester D. Myers It is certified that error appears in the above-identified patent and that said Letters Patent is hereby corrected as shown below:

<u>Column 40,</u>
Line 58, reading:
"said comestible comprised of at least one first material in"
should read:
-- said comestible comprised of a dispersion of at least one first material in --

Signed and Sealed this

Eighth Day of July, 2003

JAMES E. ROGAN
*Director of the United States Patent and Trademark Office*